United States Patent [19]

Gethner et al.

[11] Patent Number: 5,446,681
[45] Date of Patent: Aug. 29, 1995

[54] METHOD OF ESTIMATING PROPERTY AND/OR COMPOSITION DATA OF A TEST SAMPLE

[75] Inventors: Jon S. Gethner, Scotch Plains; Terry R. Todd, Budd Lake; James M. Brown, Flemington, all of N.J.

[73] Assignee: Exxon Research and Engineering Company, Florham Park, N.J.

[21] Appl. No.: 300,016

[22] Filed: Sep. 2, 1994

Related U.S. Application Data

[63] Continuation of Ser. No. 990,715, Dec. 15, 1992, abandoned, which is a continuation of Ser. No. 596,435, Oct. 12, 1990, abandoned.

[51] Int. Cl.$^6$ .............................................. G06F 15/20
[52] U.S. Cl. ................................. 364/554; 364/571.01; 364/571.04; 364/498
[58] Field of Search ................... 364/554, 498, 577.01, 364/571.04, 578

[56] References Cited

U.S. PATENT DOCUMENTS

| | | | |
|---|---|---|---|
| 4,864,842 | 9/1989 | Regimand | 364/571.02 |
| 4,866,644 | 9/1989 | Shenk et al. | 364/571.02 |
| 4,959,796 | 9/1990 | Hidaka et al. | 364/496 |
| 5,121,337 | 6/1992 | Brown | 364/498 |
| 5,243,546 | 9/1993 | Maggard | 364/571.02 |

*Primary Examiner*—Ellis B. Ramirez
*Attorney, Agent, or Firm*—Ronald D. Hantman

[57] ABSTRACT

A method of operating a spectrometer to determine property and/or composition data of a sample comprises an on-line spectral measurement of the sample using a computer controlled spectrometer, statistical analysis of the sample data based upon a statistical model using sample calibration data, and automatically identifying a sample if necessary based upon statistical and expert system (rule-based) criteria. Sample collection based upon statistical criteria consists of performing a statistical or rule-based check against the model to identify measurement data which are indicative of chemical species not in the samples already stored in the model. Samples identified either by a statistical criteria or using an expert system (rule-based decisions) are used preferably to isolate the liquid sample using a computer controlled automatic sampling system. The samples can be saved for subsequent laboratory analysis in removable sample containers. The results of the laboratory analysis together with the on-line spectroscopic measurements are preferably used to update the model being used for the analysis.

12 Claims, 2 Drawing Sheets

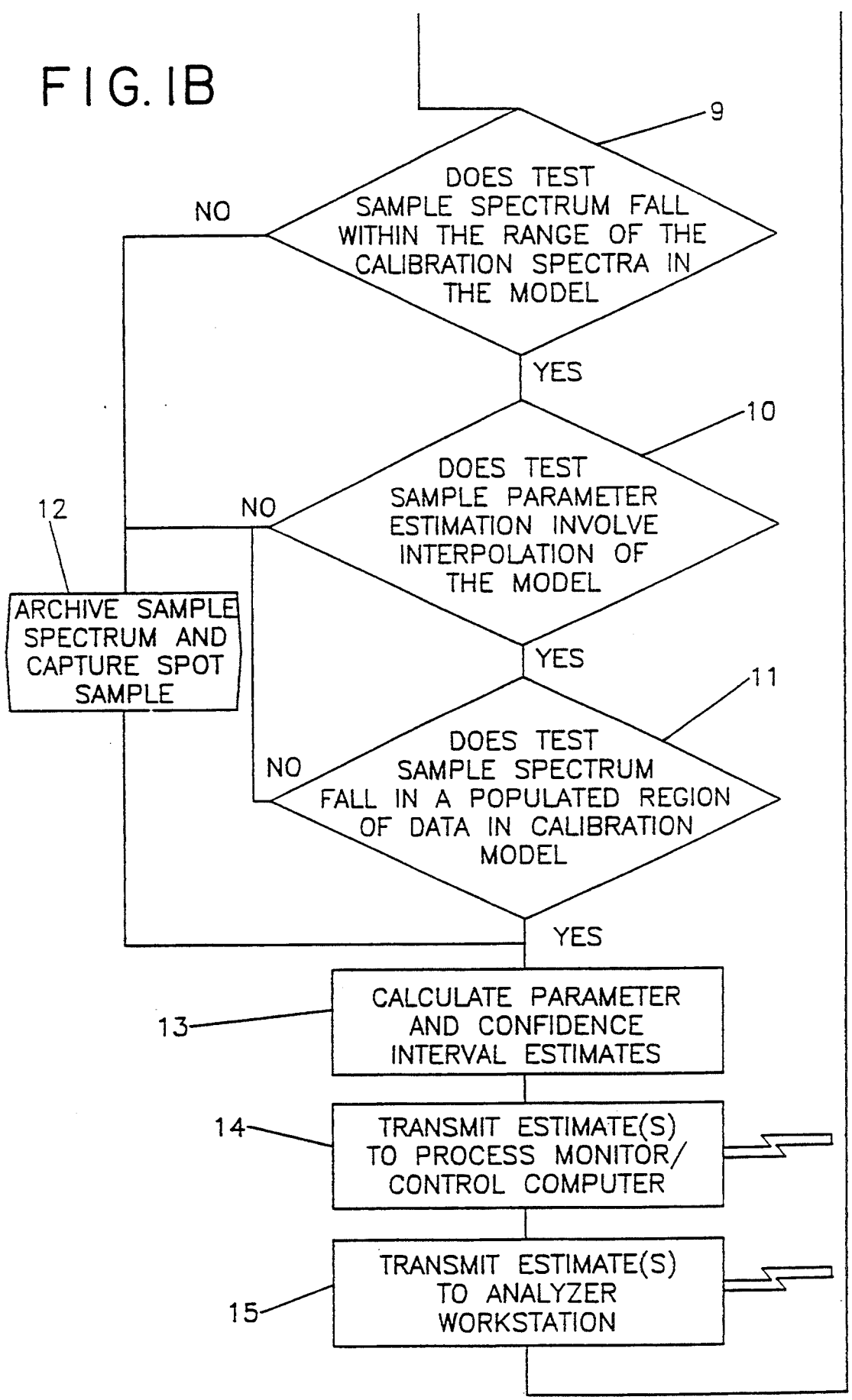

METHOD OF ESTIMATING PROPERTY AND/OR COMPOSITION DATA OF A TEST SAMPLE

This is a continuation of application Ser. No. 07-990715, filed on Dec. 15, 1992, which is a continuation of Ser. No. 07/596,435 filed on Oct. 12, 1990 which are both abandoned.

FIELD OF THE INVENTION

This invention relates to a method of estimating unknown property and/or composition data (also referred to herein as "parameters") of a sample. Examples of property and composition data are chemical composition measurements (such as the concentration of individual chemical components as, for example, benzene, toluene, xylene, or the concentrations of a class of compounds as, for example, paraffins), physical property measurements (such as density, index of refraction, hardness, viscosity, flash point, pour point, vapor pressure), performance property measurement (such as octane number, cetane number, combustibility), and perception (smell/odor, color).

BACKGROUND OF THE INVENTION

The infrared (12500—400 cm$^{-1}$) spectrum of a substance contains absorption features due to the molecular vibrations of the constituent molecules. The absorptions arise from both fundamentals (single quantum transitions occurring in the mid-infrared region from 4000—400 cm$^{-1}$) and combination bands and overtones (multiple quanta transitions occurring in the mid- and the near-infrared region from 12500—4000 cm$^{-1}$). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties requires that a calibration be performed to establish the relationship between the absorbances and the component or property that is to be estimated. For complex mixtures, where considerable overlap between the absorptions of individual constituents occurs, such calibrations must be accomplished using multivariate data analysis methods.

In complex mixtures, each constituent generally gives rise to multiple absorption features corresponding to different vibrational motions. The intensities of these absorptions will all vary together in a linear fashion as the concentration of the constituent varies. Such features are said to have intensities which are correlated in the frequency (or wavelength) domain. This correlation allows these absorptions to be mathematically distinguished from random spectral measurement noise which shows no such correlation. The linear algebra computations which separate the correlated absorbance signals from the spectral noise form the basis for techniques such as Principal Components Regression (PCR) and Partial Least Squares (PLS). As is well known in the art, PCR is essentially the analytical mathematical procedure of Principal Components Analysis (PCA) followed by regression analysis. Reference is directed to "An Introduction to Multivariate Calibration and Analysis", Analytical Chemistry, Vol. 59, No. 17, Sep. 1, 1987, pages 1007 to 1017, for an introduction to multiple linear regression (MLR), PCR and PLS.

PCR and PLS have been used to estimate elemental and chemical compositions and to a lesser extent physical or thermodynamic properties of solids and liquids based on their mid-or near-infrared spectra. These methods involve: [1] the collection of mid- or near-infrared spectra of a set of representative samples; [2] mathematical treatment of the spectral data to extract the Principal Components or latent variables (e.g. the correlated absorbance signals described above); and [3] regression of these spectral variables against composition and/or property data to build a multivariate model. The analysis of new samples then involves the collection of their spectra, the decomposition of the spectra in terms of the spectral variables, and the application of the regression equation to calculate the composition/-properties.

Providing the components of the sample under test are included in the calibration samples used to build the predictive model, then, within the limits of the inherent accuracy of the predictions obtainable from the model, an accurate estimate of the property and/or composition data of the test sample will be obtained from its measured spectrum. However, if one or more of the components of the test sample are not included in the calibration samples on which the model is based, then prediction of the property and/or composition data will be inaccurate, because the predictive model produces a "best fit" of the calibration data to the test sample where some of the calibration data is inappropriate for that test sample. The present invention addresses, and seeks to overcome, this problem.

SUMMARY OF THE INVENTION

The method of the present invention is for estimating property and/or composition data of a test sample. An application of particular practical importance is the analysis of hydrocarbon test samples or for ascertaining the hydrocarbon content of a hydrocarbon/water mixture, whether in phase separated or emulsion form. The inventive method involves a number of steps. Firstly, a spectral measurement is performed on the test sample. Then, property and/or composition data of the test sample can be estimated from its measured spectrum on the basis of a predictive model correlating calibration sample spectra to known property and/or compositistion data of those calibration samples. In the present method, a determination is made, on the basis of a check of the measured spectrum against the predictive model, as to whether or not the measured spectrum is within the range of calibration sample spectra in the model. If the result of the check is negative, a response is generated, accordingly.

In this way, if the result of the check is affirmative (i.e., the measured spectrum is indicative of chemical compositions encompassed by the samples included in the predictive model), then the person performing the analysis can be satisfied that the corresponding property and/or composition prediction is likely to be accurate (of course within the limits of the inherent accuracy of the predictive model). However, even then, further tests may be made to optimize the effectiveness of the checking of the sample under test, in order to increase the confidence level of the prediction made for each test sample which passes all the tests. This preferred way of performing the invention will be described in more detail hereinbelow. Correspondingly, if the result of the check is negative, then the analyst knows that any corresponding prediction is likely to provide unreliable results.

The response to a negative result of the check can take one of many forms. For example, it could be simply to provide a warning or alarm to the operator. The prediction of property and/or composition data can be made even when a warning or alarm is generated, but the warning or alarm indicates to the analyst that the prediction is likely to be unreliable. Preferably, any test sample for which the result of the check is negative (i.e. the measures spectrum is not within the range of calibration sample spectra in the model) is physically isolated. It can then be taken to the laboratory for independent analysis of its property and/or composition (determined by the standard analytical technique used in generating the property and/or composition data for the initial model). Preferably, the model is adapted to allow the data separately determined in this way, together with the corresponding measured spectral data, to be entered into the model database, so that the model thereby becomes updated with this additional data, so as to enlarge the predictive capability of the model. In this way, the model "learns" from identification of a test sample for which it cannot perform a reliable prediction, so that next time a similar sample is tested containing chemical species of the earlier sample (and assuming any other chemical species it contains correspond to those of other calibration samples in the model), a reliable prediction of property and/or composition data for that similar sample will be made.

Various forms of predictive model are possible for determining the correlation between the spectra of the calibration samples and their known property and/or composition data. Thus, the predictive model can be based on principal components analysis or partial least squares analysis of the calibration sample spectra. In any eigenvector-based predictive model such as the foregoing, whether or not the measured spectrum of the test sample is within the range of the calibration sample spectra in the model can be determined in the following manner. A simulated spectrum for the test sample is determined by deriving coefficients for the measured test spectrum from the dot (scalar) products of the measured test spectrum with each of the model eigenspectra and by adding together the model eigenspectra scaled by the corresponding coefficient. Then, a comparison is made between the simulated spectrum calculated in this way and the measured spectrum as an estimate of whether or not the measured spectrum is within the range of the calibration sample spectra in the model. This comparison, according to a preferred way of performing the invention, can be made by determining a residual spectrum as the difference between the simulated spectrum and the measured spectrum, by calculating the Euclidean norm by summing the squares of the magnitudes of the residual spectrum at discrete frequencies, and by evaluating the magnitude of the Euclidean norm. A large value, determined with reference to a preselected threshold distance, is indicative that the required data prediction of the test sample cannot accurately be made, while a Euclidean norm lower than the threshold indicates an accurate prediction can be made.

The preferred way of performing the invention described above employs a statistical validity check against the predictive model. However, as an alternative to a statistical check, a rule-based check may be made. Examples of rule-based checks are pattern recognition techniques and/or comparison with spectra of computerized spectral libraries.

The calibration sample spectra may contain spectral data due to the measurement process itself e.g. due to baseline variations and/or ex-sample interferences (such as due to water vapor or carbon dioxide). This measurement process spectral data can be removed from the calibration sample spectra prior to defining the predictive model by orthogonalizing the calibration sample spectra to one or more spectra modeling the measurement process data. This will be described in further detail herein below under the heading "CONSTRAINED PRINCIPAL SPECTRA ANALYSIS (CPSA)".

Even though a test sample has passed the above-described validity check, further checking may be desirable. For example, despite passing the validity check, the property and/or compositions data prediction may be an extrapolation from the range of data covered by the calibration samples used for forming the predictive model. It is therefore preferred that the Mahalanobis distance is determined for the measured spectrum and the test sample "accepted" from this further test if the magnitude of the Mahalanobis distance is below an appropriate predetermined amount selected by the analyst. If the calculated Mahalanobis distance is above the appropriate predetermined amount, a similar response as described hereinabove for a negative check is initiated.

Another statistical check is to ascertain whether the test sample is lying in a region in which the number of calibration samples in the predictive model is sparse. This check can be made by calculating the Euclidean norm derived for each test sample/calibration sample pair and comparing the calculated Euclidean norms with a threshold value which, if exceeded, indicates that the sample has failed to pass this additional statistical check. In which case, a similar response as described hereinabove for a negative check is initiated.

The method disclosed herein finds particular application to on-line estimation of property and/or composition data of hydrocarbon test samples. Conveniently and suitably, all or most of the above-described steps are performed by a computer system of one or more computers with minimal or no operator interaction required.

It has been remarked above that the prediction can be based on principal components analysis, and also that spectral data in the calibration sample spectra due to measurement process data itself can be removed by an orthogonalization procedure. The combination of principal components analysis and the aforesaid orthogonalization procedure is referred to herein as Constrained Principal Spectra Analysis, abbreviated to "CPSA". The present invention can employ any numerical analysis technique (such as PCR, PLS or MLK) through which the predictive model can be obtained to provide an estimation of unknown property and/or composition data. It is preferred that the selected numerical analysis technique be CPSA. CPSA is described in detail in the present assignees U.S. patent application Ser. No. 07/597,910 of James M. Brown, filed on Oct. 15, 1990 (now U.S. Pat. No. 5,121,337), the contents of which are expressly incorporated herein by reference. The relevant disclosure of this patent application of James M. Brown will be described below.

In another aspect, the invention provides apparatus for estimating property and/or composition data of a hydrocarbon test sample. The apparatus comprises spectrometer means for performing a spectral measurement on a test sample, and also computer means. The computer means serves three main purposes. The first is for estimating the property and/or composition data of the test sample from its measured spectrum on the basis of a predictive model correlating calibration sample spectra to known property and/or composition data for those calibration samples. The second is for determining, on the basis of a check (such as described hereinabove) of the measured spectrum against the predictive model, whether or not the measured spectrum is within the range of the calibration sample spectra in the model. The third function of the computer means is for generating a response (the nature of which has been described hereinabove in detail with reference to the inventive method) if the result of the check is negative.

The computer means is generally arranged to determine the predictive model according to all the calibration sample spectra data and all the known property and/or composition data of the calibration samples in its database. The computer means may be further arranged to respond to further such data inputted to its database for storage therein, so that the predictive model thereby becomes updated according to the further such data. The inputted property and/or composition data is derived by a separate method, such as by laboratory analysis.

The Constrained Principal Spectra Analysis (CPSA), being a preferred implementation of the inventive method and apparatus, will now be described in detail.

CONSTRAINED PRINCIPAL SPECTRA ANALYSIS (CPSA)

In CPSA, the spectral data of a number (n) of calibration samples is corrected for the effects of data arising from the measurement process itself (rather than from the sample components). The spectral data for n calibration samples is quantified at f discrete frequencies to produce a matrix X (of dimension f by n) of calibration data. The first step in the method involves producing a correction matrix U of dimension f by m comprising m digitized correction spectra at the discrete frequencies f, the correction spectra simulating data arising from the measurement process itself. The other step involves orthoganalizing X with respect to U to produce a corrected spectra matrix $X_c$ whose spectra are orthogonal to all the spectra in U. Due to this orthogonality, the spectra in matrix $X_c$ are statistically independent of spectra arising from the measurement process itself. If (as would normally be the case) the samples are calibration samples used to build a predictive model interrelating known property and composition data of the n samples and their measured spectra so that the model can be used to estimate unknown property and/or composition data of a sample under consideration from its measured spectrum, the estimated property and/or composition data will be unaffected by the measurement process itself. In particular, neither baseline variations nor spectra due for example to water vapor or carbon dioxide vapor in the atmosphere of the spectrometer will introduce any error into the estimates. It is also remarked that the spectra can be absorption spectra and the preferred embodiments described below all involve measuring absorption spectra. However, this is to be considered as exemplary and not limiting on the scope of the invention as defined by the appended claims, since the method disclosed herein can be applied to other types of spectra such as reflection spectra and scattering spectra (such as Raman scattering). Although the description given herein relates to NIR (near-infrared) and MIR (mid-infrared), nevertheless, it will be understood that the method finds applications in other spectral measurement wavelength ranges including, for example, ultraviolet, visible spectroscopy and Nuclear Magnetic Resonance (NMR) spectroscopy.

Generally, the data arising from the measurement process itself are due to two effects. The first is due to baseline variations in the spectra. The baseline variations arise from a number of causes such as light source temperature variations during the measurement, reflectance, scattering or absorbances from the cell windows, and changes in the temperature (and thus the sensitivity) of the instrument detector. These baseline variations generally exhibit spectral features which are broad (correlate over a wide frequency range). The second type of measurement process signal is due to ex-sample chemical compounds present during the measurement process, which give rise to sharper line features in the spectrum. For current applications, this type of correction generally includes absorptions due to water vapor and/or carbon dioxide in the atmosphere in the spectrometer. Absorptions due to hydroxyl groups in optical fibers could also be treated in this fashion. Corrections for contaminants present in the samples can also be made, but generally only in cases where the concentration of the contaminant is sufficiently low as to not significantly dilute the concentrations of the sample components, and where no significant interactions between the contaminant and sample component occurs. It is important to recognize that these corrections are for signals that are not due to components in the sample. In this context, "sample" refers to that material upon which property and/or component concentration measurements are conducted for the purpose of providing data for the model development. By "contaminant," we refer to any material which is physically added to the sample after the property/component measurement but before or during the spectral measurement.

The present corrective method can be applied to correct only for the effect of baseline variations, in which case these variations can be modeled by a set of preferably orthogonal, frequency (or wavelength) dependent polynomials which form the matrix U of dimension f by m where m is the order of the polynomials and the columns of U are preferably orthogonal polynomials, such as Legendre polynomials. Alternatively the corrective method can be applied to correct only for the effect of ex-sample chemical compounds (e.g. due to the presence in the atmosphere of carbon dioxide and/or water vapor). In this case, the spectra that form the columns of U are preferably orthogonal vectors that are representative of the spectral interferences produced by such chemical compounds. It is preferred, however, that both baseline variations and ex-sample chemical compounds are modelled in the manner described to form two correction matrices $U_p$ of dimension f by p and $X_s$, respectively. These matrices are then combined into the single matrix U, whose columns are the columns of $U_p$ and $X_s$ arranged side-by-side.

In a preferred way of performing the invention, in addition to matrix X of spectral data being orthogonalized relative to the correction matrix U, the spectra or columns of U are all mutually orthogonal. The production of the matrix U having mutually orthogonal spectra or columns can be achieved by firstly modeling the baseline variations by a set of orthogonal frequency (or wavelength) dependent polynomials which are computer generated simulations of the baseline variations and form the matrix $U_p$, and then at least one, and usually a plurality, of spectra of ex-sample chemical compounds (e.g. carbon dioxide and water vapor) which are actual spectra collected on the instrument, are supplied to form the matrix $X_s$. Next the columns of $X_s$ are orthogonalized with respect to $U_p$ to form a new matrix $X_s'$. This removes baseline effects from ex-sample chemical compound corrections. Then, the columns of $X_s'$ are orthogonalized with respect to one another to form a new matrix $U_s$, and lastly $U_p$ and $U_s$ are combined to form the correction matrix U , whose columns are the columns of $U_p$ and $U_s$ arranged side-by-side. It would be possible to change the order of the steps such that firstly the columns of $X_s$ are orthogonalized to form a new matrix of vectors and then the (mutually orthogonal) polynomials forming the matrix $U_p$ are orthogonalized relative to these vectors and then combined with them to form the correction matrix U . However, this is less preferred because it defeats the advantage of generating the polynomials as being orthogonal in the first place, and it will also mix the baseline variations in with the spectral variations due to ex-sample chemical compounds and make them less useful as diagnostics of instrument performance.

In a real situation, the sample spectral data in the matrix X will include not only spectral data due to the measurement process itself but also data due to noise. Therefore, once the matrix X (dimension f by n) has been orthogonalized with respect to the correction matrix U (dimension f by m), the resulting corrected spectral matrix $X_c$ will still contain noise data. This can be removed in the following way. Firstly, a singular value decomposition is performed on matrix $X_c$ in the form $X_c = U\Sigma V^t$, where U is a matrix of dimension f by n and contains the principal component spectra as columns, $\Sigma$ is a diagonal matrix of dimension n by n and contains the singular values, and V is a matrix of dimension n by n and contains the principal component scores, $V^t$ being the transpose of V. In general, the principal components that correspond to noise in the spectral measurements in the original n samples will have singular values which are small in magnitude relative to those due to the wanted spectral data, and can therefore be distinguished from the principal components due to real sample components. Accordingly, the next step in the method involves removing from U, $\Sigma$ and V the $k+1$ through n principal components that correspond to the noise, to form the new matrices $U'$, $\Sigma'$ and $V'$ of dimensions f by k, k by k and n by k, respectively. When these matrices are multiplied together, the resulting matrix, corresponding with the earlier corrected spectra matrix $X_c$, is free of spectral data due to noise.

For the selection of the number (k) of principal components to keep in the model, a variety of statistical tests suggested in the literature could be used but the following steps have been found to give the best results. Generally, the spectral noise level is known from experience with the instrument. From a visual inspection of the eigenspectra (the columns of matrix U resulting from the singular value decomposition), a trained spectroscopist can generally recognize when the signal levels in the eigenspectra are comparable with the noise level. By visual inspection of the eigenspectra, an approximate number of terms, k, to retain can be selected. Models can then be built with, for example, $k-2$, $k-1$, k, $k+1$, $k+2$ terms in them and the standard errors and PRESS (Predictive Residual Error Sum of Squares) values are inspected. The smallest number of terms needed to obtain the desired precision in the model or the number of terms that give the minimum PRESS value is then selected. This choice is made by the spectroscopist, and is not automated. A Predicted Residual Error Sum of Squares is calculated by applying a predictive model for the estimation of property and/or component values for a test set of samples which were not used in the calibration but for which the true value of the property or component concentration is known. The difference between the estimated and true values is squared, and summed for all the samples in the test set (the square root of the quotient of the sum of squares and the number of test samples is sometimes calculated to express the PRESS value on a per sample basis). A PRESS value can be calculated using a cross validation procedure in which one or more of the calibration samples are left out of the data matrix during the calibration, and then analyzed with the resultant model, and the procedure is repeated until each sample has been left out once.

The polynomials that are used to model background variations are merely one type of correction spectrum. The difference between the polynomials and the other "correction spectra" modeling ex-sample chemical compounds is twofold. First, the polynomials may conveniently be computer-generated simulations of the background (although this is not essential and they could instead be simple mathematical expressions or even actual spectra of background variations) and can be generated by the computer to be orthogonal. The polynomials may be Legendre polynomials which are used in the actual implementation of the correction method since they save computation time. There is a specific recursive algorithm to generate the Legendre polynomials that is disclosed in the description hereinafter. Generally, each row of the $U_p$ matrix corresponds to a given frequency (or wavelength) in the spectrum. The columns of the $U_p$ matrix will be related to this frequency. The elements of the first column would be a constant, the elements of the second column would depend linearly on the frequency, the elements of the third column would depend on the square of the frequency, etc. The exact relationship is somewhat more complicated than that if the columns are to be orthogonal. The Legendre polynomials are generated to be orthonormal, so that it is not necessary to effect a singular value decomposition or a Gram-Schmidt orthogonalization to make them orthogonal. Alternatively, any set of suitable polynomial terms could be used, which are then orthogonalized using singular value decomposition or a Gram-Schmidt orthogonalization. Alternatively, actual spectra collected on the instrument to simulate background variation can be used and orthogonalized via one of these procedures. The other "correction spectra" are usually actual spectra collected on the instrument to simulate interferences due to ex-sample chemical compounds, e.g. the spectrum of water vapor, the spectrum of carbon dioxide vapor, or the spectrum of the optical fiber of the instrument. Computer generated spectra could be used here if the spectra of water vapor, carbon dioxide, etc. can be simulated. The other difference for the implementation of the correction method is that these "correction spectra" are not orthogonal initially, and therefore it is preferred that they be orthogonalized as part of the procedure. The polynomials and the ex-sample chemical compound "correction spectra" could be combined into one matrix, and orthogonalized in one step to produce the correction vectors. In practice, however, this is not the best procedure, since the results would be sensitive to the scaling of the polynomials relative to the ex-sample chemical compound "correction spectra". If the ex-sample chemical compound "correction spectra" are collected spectra, they will include some noise. If the scaling of the polynomials is too small, the contribution of the noise in these "correction spectra" to the total variance in the correction matrix U would be larger than that of the polynomials, and noise vectors would end up being included in the ex-sample chemical compound correction vectors. To avoid this, preferably the polynomials are generated first, the ex-sample chemical compound "correction spectra" are orthogonalized to the polynomials, and then the correction vectors are generated by performing a singular value decomposition (described below) on the orthogonalized "correction spectra".

As indicated above, a preferred way of performing the correction for measurement process spectral data is firstly to generate the orthogonal set of polynomials by which model background variations, then to orthogonalize any "correction spectra" due to ex-sample chemical compounds (e.g. carbon dioxide and/or water vapor) to this set to produce a set of "correction vectors", and finally to orthogonalize the resultant "correction vectors" among themselves using singular value decomposition. If multiple examples of "correction spectra", e.g. several spectra of water vapor, are used, the final number of "correction vectors" will be less than the number of initial "correction spectra". The ones eliminated correspond with the measurement noise. Essentially, principal components analysis (PCA) is being performed on the orthogonalized "correction spectra" to separate the real measurement process data being modelled from the random measurement noise.

It is remarked that the columns of the correction matrix U do not have to be mutually orthogonal for the correction method to work, as long as the columns of the data matrix X are orthogonalized to those of the correction matrix U . However, the steps for generating the U matrix to have orthogonal columns is performed to simplify the computations required in the orthogonalization of the spectral data X of the samples relative to the correction matrix U , and to provide a set of statistically independent correction terms that can be used to monitor the measurement process. By initially orthogonalizing the correction spectra $X_s$ due to ex-sample chemical compounds to $U_p$ which models background variations, any background contribution to the resulting correction spectra is removed prior to the orthogonalization of these correction spectra among themselves. This procedure effectively achieves a separation of the effects of background variations from those of ex-sample chemical compound variations, allowing these corrections to be used as quality control features in monitoring the performance of an instrument during the measurement of spectra of unknown materials, as will be discussed hereinbelow.

When applying the technique for correcting for the effects of measurement process spectral data in the development of a method of estimating unknown property and/or composition data of a sample under consideration, the following steps are performed. Firstly, respective spectra of n calibration samples are collected, the spectra being quantified at f discrete frequencies (or wavelengths) and forming a matrix X of dimension f by n. Then, in the manner described above, a correction matrix U of dimension f by m is produced. This matrix comprises m digitized correction spectra at the discrete frequencies f, the correction spectra simulating data arising from the measurement process itself. The next step is to orthogonalize X with respect to U to produce a corrected spectra matrix $X_c$ whose spectra are each orthogonal to all the spectra in U . The method further requires that c property and/or composition data are collected for each of the n calibration samples to form a matrix Y of dimension n by c ($c \geq 1$). Then, a predictive model is determined correlating the elements of matrix Y to matrix $X_c$. Different predictive models can be used, as will be explained below. The property and/or composition estimating method further requires measuring the spectrum of the sample under consideration at the f discrete frequencies to form a matrix of dimension f by 1. The unknown property and/or composition data of the samples is then estimated from its measured spectrum using the predictive model. Generally, each property and/or component is treated separately for building models and produces a separate f by 1 prediction vector. The prediction is just the dot product of the unknown spectrum and the prediction vector. By combining all the prediction vectors into a matrix P of dimension f by c, the prediction involves multiplying the spectrum matrix (a vector of dimension f can be considered as a 1 by f matrix) by the prediction matrix to produce a 1 by c vector of predictions for the c properties and components.

As mentioned in the preceding paragraph, various forms of predictive model are possible. The predictive model can be determined from a mathematical solution to the equation $Y = X_c^t P + E$, where $X_c^t$ is the transpose of the corrected spectra matrix $X_c$, P is the predictive matrix of dimension f by c, and E is a matrix of residual errors from the model and is of dimension n by c. The validity of the equation $Y = X_c^t P + E$ follows from the inverse statement of Beer's law, which itself can be expressed in the form that the radiation-absorbance of a sample is proportional to the optical pathlength through the sample and the concentration of the radiation-absorbing species in that sample. Then, for determining the vector $y_u$ of dimension 1 by c containing the estimates of the c property and/or composition data for the sample under consideration, the spectrum $x_u$ of the sample under consideration, $x_u$ being of dimension f by 1, is measured and $y_u$ is determined from the relationship $y_u = x_u^t P$, $x_u^t$ being the transpose of matrix $x_u$.

Although, in a preferred implementation of this invention, the equation $Y = X_c^t P + E$ is solved to determine the predictive model, the invention could also be used with models whose equation is represented (by essentially the statement of Beer's law) as $X_c = AY^t + E$, where A is an f by c matrix. In this case, the matrix A would first be estimated as $A = X_c Y (Y^t Y)^{-1}$. The estimation of the vector $y_u$ of dimension 1 by c containing the c property and/or composition data for the sample under consideration from the spectrum $x_u$ of the sample under consideration would then involve using the relationship $y_u = x_u^t A (A^t A)^{-1}$. This calculation, which is a constrained form of the K-matrix method, is more restricted in application, since the required inversion of $Y^t Y$ requires that Y contain concentration values for all sample components, and not contain property data.

The mathematical solution to the equation $Y = X_c^t P + E$ (or $X_c = AY^t + E$) can be obtained by any one of a number of mathematical techniques which are known per se, such as linear least squares regression, sometimes otherwise known as multiple linear regression (MLR), principal components analysis/regression (PCA/PCR) and partial least squares (PLS). As mentioned above, an introduction to these mathematical techniques is given in "An Introduction to Multivariate Calibration and Analysis", Analytical Chemistry, Vol. 59, No. 17, Sep. 1, 1987, Pages 1007 to 1017.

The purpose of generating correction matrix U and in orthogonalizing the spectral data matrix X to U is twofold: Firstly, predictive models based on the resultant corrected data matrix $X_c$ are insensitive to the effects of background variations and ex-sample chemical components modeled in U, as explained above. Secondly, the dot (scaler) products generated between the columns of U and those of X contain information about the magnitude of the background and ex-sample chemical component interferences that are present in the calibration spectra, and as such, provide a measure of the range of values for the magnitude of these interferences that were present during the collection of the calibration spectral data. During the analysis of a spectrum of a material having unknown properties and/or composition, similar dot products can be formed between the unknown spectrum, $x_u$, and the columns of U, and these values can be compared with those obtained during the calibration as a means of checking that the measurement process has not changed significantly between the time the calibration is accomplished and the time the prodictive model is applied for the estimation of properties and components for the sample under test. These dot products thus provide a means of performing a quality control assessment on the measurement process.

The dot products of the columns of U with those of the spectral data matrix X contain information about the degree to which the measurement process data contribute to the individual calibration spectra. This information is generally mixed with information about the calibration sample components. For example, the dot product of a constant vector (a first order polynomial) will contain information about the total spectral integral, which is the sum of the integral of the sample absorptions, and the integral of the background. The information about calibration sample components is, however, also contained in the eigenspectra produced by the singular value decomposition of $X_c$. It is therefore possible to remove that portion of the information which is correlated to the sample components from the dot products so as to recover values that are uncorrelated to the sample components, i.e. values that represent the true magnitude of the contributions of the measurement process signals to the calibration spectra. This is accomplished by the following steps:

(1) A matrix V of dimension n by m is formed as the product of $X^t U$, the individual elements of V being the dot products of the columns of X with those of U;

(2) The corrected data matrix $X_c$ is formed, and its singular value decomposition is computed as $U \Sigma V^t$;

(3) A regression of the form $V = VZ + R$ is calculated to establish the correlation between the dot products and the scores of the principal components: VZ represents the portion of the dot products which is correlated to the sample components and the regression residuals R represent the portion of the dot products that are uncorrelated to the sample components, which are in fact the measurement process signals for the calibration samples;

(4) In the analysis of a sample under test, the dot products of the unknown spectrum with each of the correction spectra (columns of U) are calculated to form a vector v, the corrected spectrum $x_c$ is calculated, the scores for the corrected spectrum are calculated as $v = x_c^t U \Sigma^{-1}$, and the uncorrelated measurement process signal values are calculated as $r = v - vZ$. The magnitude of these values is then compared to the range of values in R as a means of comparing the measurement process during the analysis of the unknown to that during the calibration.

It will be appreciated that the performance of the above disclosed correction method and method of estimating the unknown property and/or composition data of the sample under consideration involves extensive mathematical computations to be performed. In practice, such computations are made by computer means comprising a computer or computers, which is connected to the instrument. In a measurement mode, the computer means receives the measured output spectrum of the calibration sample, ex-sample chemical compound or test sample. In a correction mode in conjunction with the operator, the computer means stores the calibration spectra to form the matrix X, calulates the correction matrix U, and orthogonalizes X with respect to the correction matrix U. In addition, the computer means operates in a storing mode to store the c known property and/or composition data for the n calibration samples to form the matrix Y of dimension n by c ($c \geq 1$). In a model building mode, the computer means determines, in conjunction with the operator, a predictive model correlating the elements of matrix Y to those of matrix $X_c$. Lastly, the computer means is arranged to operate in a prediction mode in which it estimates the unknown property and/or compositional data of the sample under consideration from its measured spectrum using the determined predictive model correlating the elements of matrix Y to those of matrix $X_c$.

In more detail, the steps involved according to a preferred way of making a prediction of property and/or composition data of a sample under consideration can be set out as follows. Firstly, a selection of samples for the calibration is made by the operator or a laboratory technician. Then, in either order, the spectra and properties/composition of these samples need to be measured, collected and stored in the computer means by the operator and/or laboratory technician, together with spectra of ex-sample chemical compounds to be used as corrections. In addition, the operator selects the computer-generated polynomial corrections used to model baseline variations. The computer means generates the correction matrix U and then orthogonalizes the calibration sample spectra (matrix X) to produce the corrected spectral matrix $X_c$ and, if PCR is used, performs the singular value decomposition on matrix $X_c$. The operator has to select (in PCR) how many of the principal components to retain as correlated data and how many to discard as representative of (uncorrelated) noise. Alternatively, if the PLS technique is employed, the operator has to select the number of latent variables to use. If MLR is used to determine the correlation between the corrected spectral matrix $X_c$ and the measured property and/or composition data Y, then a selection of frequencies needs to be made such that the number of frequencies at which the measured spectra are quantized is less than the number of calibration samples. Whichever technique is used to determine the correlation (i.e. the predictive model) interrelating $X_c$ and Y, having completed the calibration, the laboratory technician measures the spectrum of the sample under consideration which is used by the computer means to compute predicted property and/or composition data based on the predictive model.

Mathematical Basis for CPSA

The object of Principal Components Analysis (PCA) is to isolate the true number of independent variables in the spectral data so as to allow for a regression of these variables against the dependent property/composition variables. The spectral data matrix, X, contains the spectra of the n samples to be used in the calibration as columns of length f, where f is the number of data points (frequencies or wavelengths) per spectrum. The object of PCA is to decompose the f by n X matrix into the product of several matrices. This decomposition can be accomplished via a Singular Value Decomposition:

$$X = U\Sigma V^t \quad (1)$$

where U (the left eigenvector matrix) is of dimension f by n, $\Sigma$ (the diagonal matrix containing the singular values $\sigma$) is of dimension n by n, and $V^t$ is the transpose of V (the right eigenvector matrix) which is of dimension n by n. Since some versions of PCA perform the Singular Value Decomposition on the transpose of the data matrix, $X^t$, and decompose it as $V\Sigma U^t$, the use of the terms left and right eigenvectors is somewhat arbitrary. To avoid confusion, U will be referred to as the eigenspectrum matrix since the individual column-vectors of U (the eigenspectra) are of the same length, f, as the original calibration spectra. The term eigenvectors will only be used to refer to the V matrix. The matrices in the singular value decomposition have the following properties:

$$U^t U = I_n \quad (2)$$

$$VV^t = V^t V = I_n \quad (3)$$

$$X^t X = V \Lambda V^t \text{ and } XX^t = U \Lambda U^t \quad (4)$$

where $I_n$ is the n by n identify matrix, and $\Lambda$ is the matrix containing the eigenvalues, $\lambda$ (the squares of the singular values), on the diagonal and zeros off the diagonal. Note that the product $UU^t$ does not yield an identity matrix for n less than f. Equations 2 and 3 imply that both the eigenspectra and eigenvectors are orthonormal. In some version of PCA, the U and $\Sigma$ are matrices are combined into a single matrix. In this case, the eigenspectra are orthogonal but are normalized to the singular values.

The object of the variable reduction is to provide a set of independent variables (the Principal Components) against which the dependent variables (the properties or compositions) can be regressed. The basic regression equation for direct calibration is $$Y = X^t P \quad (5)$$

where Y is the n by c matrix containing the property/composition data for the n samples and c properties/components, and P is the f by c matrix of regression coefficients which relate the property/composition data to the spectral data. We will refer to the c columns of P as prediction vectors, since during the analysis of a spectrum x (dimension f by 1), the prediction of the properties/components (y of dimension 1 by c) for the sample is obtained by $$y = x^t P \quad (6)$$

Note that for a single property/component, the prediction is obtained as the dot product of the spectrum of the unknown and the prediction vector. The solution to equation 5 is $$[X^t]^{-1} Y = [X^t]^{-1} X^t P = P \quad (7)$$

where $[X^t]^{-1}$ is the inverse of the $X^t$ matrix. The matrix $X^t$ is of course non-square and rank deficient (f>n), and cannot be directly inverted. Using the singular value decompositions, however, the inverse can be approximated as $$[X^t]^{-1} = U\Sigma^{-1} V^t \quad (8)$$

where $\Sigma^{-1}$ is the inverse of the square singular value matrix and contains $1/\sigma$ on the diagonal. Using equations 7 and 8, the prediction vector matrix becomes $$P = U\Sigma^{-1} V^t Y \quad (9)$$

As was noted previously, the objective of the PCA is to separate systematic (frequency correlated) signal from random noise. The eigenspectra corresponding to the larger singular values represent the systematic signal, while those corresponding to the smaller singular values represent the noise. In general, in developing a stable model, these noise components will be eliminated from the analysis before the prediction vectors are calculated. If the first k<n eigenspectra are retained, the matrices in equation 1 become U' (dimension f by k), $\Sigma'$ (dimension k by k) and V' (dimension n by k).

$$X = U'\Sigma' V'^t + E \quad (10)$$

where E is an f by n error matrix. Ideally, if all the variations in the data due to sample components are accounted for in the first k eigenspectra, E contains only random noise. It should be noted that the product $V'V'^t$ no longer yields an identity matrix. To simplify notation the ' will be dropped, and U,$\Sigma$ and V will henceforth refer to the rank reduced matrices. The choice of k, the number of eigenspectra to be used in the calibration, is based on statistical tests and some prior knowledge of the spectral noise level.

Although the prediction of a property/component requires only a single prediction vector, the calculation of uncertainties on the prediction require the full rank reduced V matrix. In practice, a two step, indirect calibration method is employed in which the singular value decomposition of the X matrix is calculated (equation 1), and then the properties/compositions are separately regressed against the eigenvectors $$Y = VB + \quad (11)$$

$$B = V^t Y \quad (12)$$

During the analysis, the eigenvector for the unknown spectrum is obtained $$v = x^t U \Sigma^{-1} \quad (13)$$

and the predictions are made as $$y = vB \quad (14)$$

The indirect method is mathematically equivalent to the direct method of equation 10, but readily provides the values needed for estimating uncertainties on the prediction.

Equation 6 shows how the prediction vector, P, is used in the analysis of an unknown spectrum. We assume that the unknown spectrum can be separated as the sum of two terms, the spectrum due to the components in the unknown, $x_c$, and the measurement process related signals for which we want to develop constraints, $x_s$. The prediction then becomes $$y = x^t P = x_c^t P + x_s^t P \quad (15)$$

If the prediction is to be insensitive to the measurement process signals, the second term in equation 15 must be zero. This implies that the prediction vector must be orthogonal to the measurement process signal spectra. From equation 10, the prediction vector is a linear combination of the eigenspectra, which in turn are themselves linear combination of the original calibration spectra ($U = XV\Sigma^{-1}$). If the original calibration spectra are all orthogonalized to a specific measurement process signal, the resulting prediction vector will also be orthogonal, and the prediction will be insensitive to the measurement process signal. This orthogonalization procedure serves as the basis for the Constrained Principal Spectra Analysis algorithm.

In the Constrained Principal Spectra Analysis (CPSA) program, two types of measurement process signals are considered. The program internally generates a set of orthonormal, frequency dependent polynomials, $U_p$. $U_p$ is a matrix of dimension f by p where p is the maximum order (degree minum one) of the polynomials, and it contains columns which are orthonormal Legendre polynomials defined over the spectral range used in the analysis. The polynomials are intended to provide constraints for spectral baseline effects. In addition, the user may supply spectra representative of other measurement process signals (e.g. water vapor spectra). These correction spectra (a matrix $X_s$ of dimension f by s where s is the number of correction spectra) which may include multiple examples of a specific type of measurement process signal, are first orthogonalized relative to the polynomials via a Gram-Schmidt orthogonalization procedure $$X_s' = X_s - U_p(U_p^t X_s) \quad (16)$$

A Singular Value Decomposition of the resultant correction spectra is then performed, $$X_s' = U_s \Sigma_s V_s^t \quad (17)$$

to generate a set of orthonormal correction eigenspectra, $U_s$. The user selects the first s' terms corresponding to the number of measurement related signals being modeled, and generates the full set of correction terms, U , which includes both the polynomials and selected correction eigenspectra. These correction terms are then removed from the calibration data, again using a Gram-Schmidt orthogonalization procedure $$X_c = X - U_m(U_m^t X) \quad (17)$$

The Principal Components Analysis of the corrected spectra, $X_c$, then proceeds via the Singular Value Decomposition $$X_c = U_c \Sigma_c V_c^t \quad (18)$$

and the predictive model is developed using the regression $$Y = V_c B \quad (19)$$

The resultant prediction vector $$P_c = U_c \Sigma_c^{-1} V_c^t Y \quad (20)$$

is orthogonal to the polynomial and correction eigenspectra, $U_m$. The resulting predictive model is thus insensitive to the modeled measurement process signals. In the analysis of an unknown, the contributions of the measurement process signals to the spectrum can be calculated as $$v = \Sigma^{-1} U^t x \quad (21)$$

and these values can be compared against the values for the calibration, V , to provide diagnostic as to whether the measurement process has changed relative to the calibration.

The results of the procedure described above are mathematically equivalent to including the polynomial and correction terms as spectra in the data matrix, and using a constrained least square regression to calculate the B matrix in equation 12. The constrained least square procedure is more sensitive to the scaling of the correction spectra since they must account for sufficient variance in the data matrix to be sorted into the k eigenspectra that are retained in the regression step. By orthogonalizing the calibration spectra to the correction spectra before calculating the singular value decomposition, we eliminate the scaling sensitivity.

Development of Empirical Model in CPSA

The Constrained Principal Spectra Analysis method allows measurement process signals which are present in the spectra of the calibration samples, or might be present in the spectra of samples which are latter analyzed, to be modeled and removed from the data (via a Gram-Schmidt orthogonalization procedure) prior to the extraction of the spectral variables which is performed via a Singular Value Decomposition (16). The spectral variables thus obtained are first regressed against the pathlengths for the calibration spectra to develop a model for independent estimation of pathlength. The spectral variables are rescaled to a common pathlength based on the results of the regression and then further regressed against the composition/property data to build the empirical models for the estimation of these parameters. During the analysis of new samples, the spectra are collected and decomposed into the constrained spectral variables, the pathlength is calculated and the data is scaled to the appropriate pathlength, and then the regression models are applied to calculate the composition/property data for the new materials. The orthogonalization procedure ensures that the resultant measurements are constrained so as to be insensitive (orthogonal) to the modeled measurement process signals. The internal pathlength calculation and renormalization automatically corrects for pathlength or flow variations, thus minimizing errors due to data scaling.

The development of the empirical model consists of the following steps:

(1.1) The properties and/or component concentrations for which empirical models are to be developed are independently determined for a set of representative samples, e.g the calibration set. The independent measurements are made by standard analytical tests including, but not limited to: elemental compositional analysis (combustion analysis, X-ray fluorescence, broad line NMR); component analysis (gas chromatography, mass spectroscopy); other spectral measurements (IR, UV/visible, NMR, color); physical property measurements (API or specific gravity, refractive index, viscosity or viscosity index); and performance property measurements (octane number, cetane number, combustibility). For chemicals applications where the number of sample components is limited, the compositional data may reflect weights or volumes used in preparing calibration blends.

(1.2) Absorption spectra of the calibration samples are collected over a region or regions of the infrared, the data being digitized at discrete frequencies (or wavelengths) whose separation is less than the width of the absorption features exhibited by the samples.

(2.0) The Constrained Principal Spectra Analysis (CPSA) algorithm is applied to generate the empirical model. The algorithm consists of the following 12 steps:

(2.1) The infrared spectral data for the calibration spectra is loaded into the columns of a matrix X, which is of dimension f by n where f is the number of frequencies or wavelengths in the spectra, and n is the number of calibration samples.

(2.2) Frequency dependent polynomials, $U_p$, (a matrix whose columns are orthonormal Legendre polynomials having dimension f by p where p is the maximum order of the polynomials) are generated to model possible variations in the spectral baseline over the spectral range used in the analysis.

(2.3) Spectra representative of a other types of measurement process signals (e.g. water vapor spectra, carbon dioxide, etc.) are loaded into a matrix $X_s$ of dimension f by s where s is the number of correction spectra used.

(2.4) The correction spectra are orthogonalized relative to the polynomials via a Gram-Schmidt orthogonalization procedure $$X_s' = X_s - U_p(U_p{}^t X_s) \qquad (2.4)$$

(2.5) A Singular Value Decomposition of the correction spectra is then performed, $$X_s' = U_s \Sigma_s V_s{}^t \qquad (2.5)$$

to generate a set of orthonormal correction eigenspectra, $U_s$. $\Sigma_s$ are the corresponding singular values, and $V_s$ are the corresponding right eigenvectors, $^t$ indicating the matrix transpose.

(2.6) The full set of correction terms, $U = U_p + U_s$, which includes both the polynomials and correction eigenspectra are then removed from the calibration data, again using a Gram-Schmidt orthogonalization procedure $$X_c = X - U (U^t X) \qquad (2.6)$$

(2.7) The Singular Value Decomposition of the corrected spectra, $X_c$, is then performed $$X_c = U_c \Sigma_c V_c{}^t \qquad (2.7)$$

(2.8) The eigenspectra from step (2.7) are examined and the a subset of the first k eigenspectra which correspond to the larger singular values in $\Sigma_c$ are retained. The k+1 through n eigenspectra which correspond to spectral noise are discarded.

$$X_c = U_k \Sigma_k V_k{}^t + E_k \qquad (2.8)$$

(2.9) The k right eigenvectors from the singular value decomposition, $V_k$, are regressed against the pathlength values for the calibration spectra, $Y_p$ (an n by 1 row vector), $$Y_p = V_k B_p + E_p \qquad (2.9a)$$

where $E_p$ is the regression error. The regression coefficients, $B_p$, are calculated as $$B_p = (V_k{}^t V_k)^{-1} V_k{}^t Y_p = V_k{}^t Y_p \qquad (2.9b)$$

(2.10) An estimation of the pathlengths for the calibration spectra is calculated as $$\hat{Y}_p = V_k B_p \qquad (2.10)$$

A n by n diagonal matrix N is then formed, the $i^{th}$ diagonal element of N being the ratio of the average pathlength for the calibration spectra, $\bar{y}_p$, divided by the estimated pathlength values for the $i^{th}$ calibration sample (the $i^{th}$ element of $\hat{Y}_p$).

(2.11) The right eigenvector matrix is then renormalized as $$V_k' = N V_k \qquad (2.11)$$

(2.12) The renormalized matrix is regressed against the properties and or concentrations, Y (Y, a n by c matrix containing the values for the n calibration samples and the c property/concentrations) to obtain the regression coefficients for the models, $$V = V_k' B + E \qquad (2.12a)$$

$$B = (V_k'{}^t V_k')^{-1} V_k' Y \qquad (2.12b)$$

(3.0) The analysis of a new sample with unknown properties/components proceeds by the following steps:

(3.1) The absorption spectrum of the unknown is obtained under the same conditions used in the collection of the calibration spectra.

(3.2) The absorption spectrum, $x_u$, is decomposed into the constrained variables, $$x_u = U_k \Sigma_k v_u{}^t \qquad (3.2a)$$

$$v_u = \Sigma^{-1} U_k{}^t x_u \qquad (3.2b)$$

(3.3) The pathlength for the unknown spectrum is estimated as $$y_p = v_u B_p \quad (3.3)$$

(3.4) The eigenvector for the unknown is rescaled as $$v_u' = v_u (y_p / \bar{y}_p) \quad (3.4)$$

where $\bar{y}_p$ is the average pathlength for the calibration spectra in (2.10).

(3.5) The properties/concentrations are estimated as $$y_u = v_u' B \quad (3.5)$$

(4.1) The spectral region used in the calibration and analysis may be limited to subregions so as to avoid intense absorptions which may be outside the linear response range of the spectrometer, or to avoid regions of low signal content and high noise.

(5.1) The samples used in the calibration may be restricted by excluding any samples which are identified as multivariate outliers by statistical testing.

(6.1) The regression in steps (2.9) and (2.12) may be accomplished via a step-wise regression (17) or PRESS based variable selection (18), so as to limit the number of variables retained in the empirical model to a subset of the first k variables, thereby eliminating variables which do not show statistically significant correlation to the parameters being estimated.

(7.1) The Mahalanobis statistic for the unknown, $D_u^2$, given by $$D_u^2 = v_u' (V_i'^t V_k')^{-1} v_u'^t \quad (7.1)$$

can be used to determine if the estimation is based on an interpolation or extrapolation of the model by comparing the value for the unknown to the average of similar values calculated for the calibration samples.

(7.2) The uncertainty on the estimated value can also be estimated based on the standard error from the regression in (2.12) and the Mahalanobis statistic calculated for the unknown.

(8.1) In the analysis of an unknown with spectrum $x_u$, the contributions of the measurement process signals to the spectrum can be calculated as $$v = \Sigma_c^{-1} U^t x_u \quad (8.1)$$

These values can be compared against the values for the calibration, V, to provide diagnostics as to whether the measurement process has changed relative to the calibration.

Those and other features and advantages of the invention will now be described, by way of example, with reference to the accompanying single drawing.

BRIEF DESCRIPTION OF THE DRAWING

The single drawing is a flow chart indicating one preferred way of performing the method of this invention.

DETAILED DESCRIPTION OF THE PREFERRED EMBODIMENT

Figure 1A:
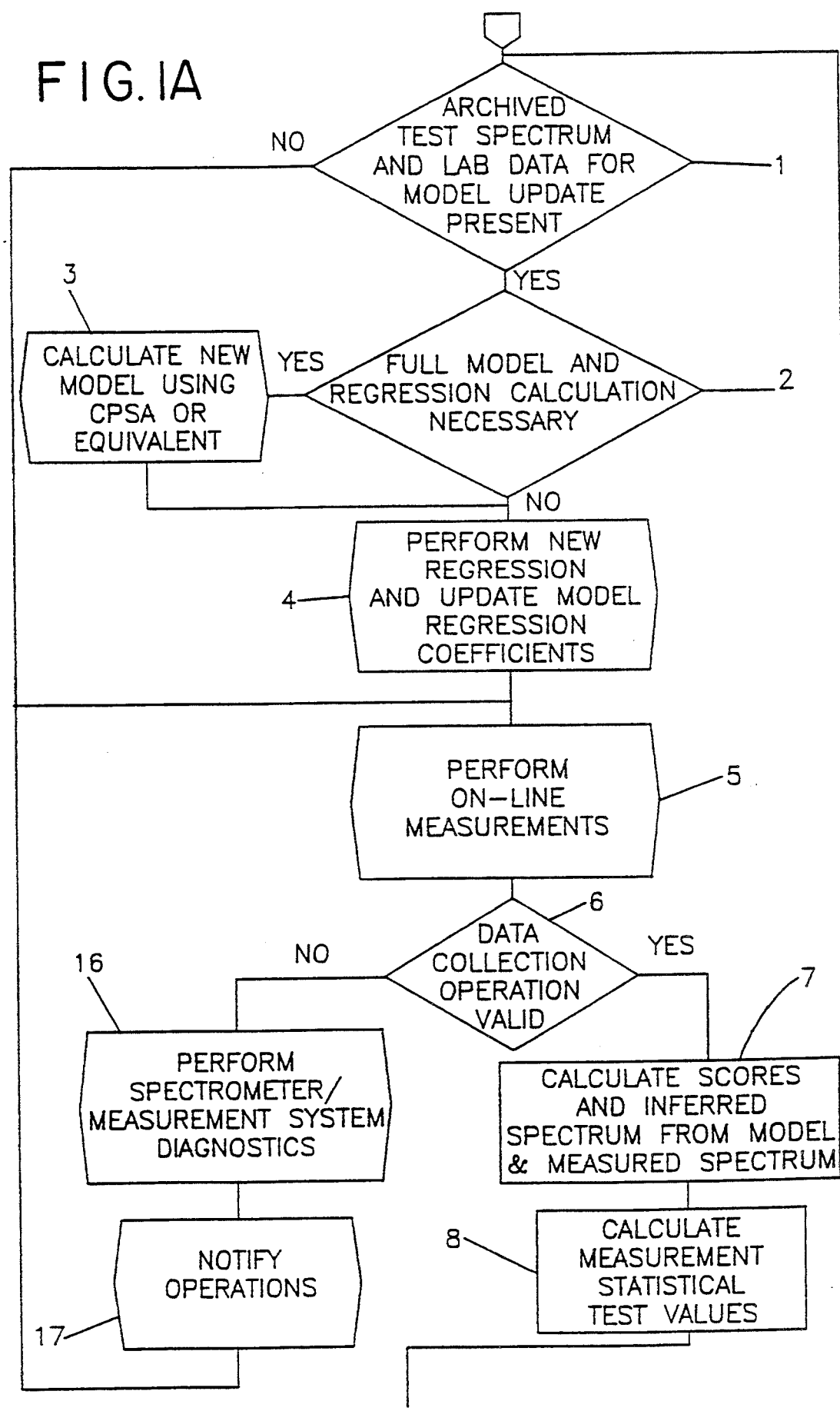

The flow chart of the single drawing gives an overview of the steps involved in a preferred way of carrying out the inventive method. The reference numerals used in the drawing relate to the method operations identified below.

1), 2), 3), and 4)

These deal with updating the estimation model and will be described later.

5) Perform On-line Measurement

An infrared absorption spectrum of the sample under consideration is measured. However, the method is applicable to any absorption spectrum. The methodology is also be applicable to a wide variety of other spectroscopic measurement techniques including ultraviolet, visible light, Nuclear Magnetic Resonance (NMR), reflection, and photoacoustic spectroscopy, etc.

The spectrum obtained from performing the on-line measurement is stored on a computer used to control the analyzer operation, and will hereafter be referred to as the test spectrum of the test sample.

6) Data Collection Operation Valid

The spectrum and any spectrometer status information that is available is examined to verify that the spectrum collected is valid from the stand point of spectrometer operations (not statistical comparison to estimation models). The principal criteria for the validity checks are that there is no apparent invalid data which may have resulted from mechanical or electronic failure of the spectrometer. Such failings can most readily be identified by examining the spectrum for unusual features including but not limited to severe baseline errors, zero data or infinite (over-range) data.

If the data collection operation is deemed to be valid, processing continues with the analysis of the data which is collected. If the data collection operation is deemed to be invalid, diagnostic routines are executed in order to perform spectrometer and measurement system diagnostics [16] (numbers in [ ] refer to operation numbers in the attached FIGURE). These may consist of specially written diagnostics or may consist of internal diagnostics contained in the spectrometer system. In either event, the results of the diagnostics are stored on the operational computer and process operations are notified that there is a potential malfunction of the spectrometer [17]. Control returns to operation [5] in order to perform the on-line measurement again since some malfunctions may be intermittent and collection of valid data may be successfully resumed upon retry.

The objective of the diagnostics performed are to isolate the cause of failure to a system module component for easy maintenance. Therefore, as part of the diagnostic procedure, it may be necessary to introduce calibration and/or standard reference samples into the sample cell in order to perform measurements under a known set of conditions which can be compared to an historical database stored on the computer. The automatic sampling system is able to introduce such samples into the sample cell upon demand from the analyzer computer.

7) Calculate Coefficients and Inferred Spectrum from Model and Measured Spectrum The measured spectrum of the sample under test, the measured spectrum being the spectral magnitudes at several discrete measurement frequencies (or wavelengths) across the frequency band of the spectrum, is used with the model to calculate several model estimation parameters which are intermediate to the calculation of the property and/or composition data parameter estimates. In the case where the model is an eigenvector-based model, such as is the case when PCA, PLS, CPSA or similar methods are used, the dot (scalar) product of the measured test spectrum with the model eigenspectra yield coefficients which are a measure of the degree to which the eigenspectra can be used to represent the test spectrum. If, in CPSA and PCR, the coefficients are further scaled by $1/\sigma$, the result would be the scores, $v_u$, defined in equation 3.2b of the foregoing section of the specification describing CPSA. Such scaling is not required in the generation of the simulated spectrum. Back calculation of the simulated test sample spectrum is performed by adding together the model eigenspectra scaled by the corresponding coefficients. For models which are not eigenvector-based methods, calculations can be defined which can be used to calculate the simulated spectrum of the test sample corresponding to the parameter estimation model.

The residual between the measured test sample spectrum and the simulated test sample spectrum is calculated at each measurement wavelength or frequency. The resulting residual spectrum is used in operation [8].

8) Calculate Measurement Statistical Test Values

From the coefficients and residual spectra available from operation [7] and the measured test sample spectrum from operation [5], several statistical test values can be calculated which are subsequently used in operations [9-11]. Preferred statistics are described in the discussion of operations [9-11] and are particularly useful for eigenvector-based methods. The calculation in the current operation is to provide statistical measures which can be used to assess the appropriateness of the model for estimating parameters for the test sample. Any method, statistical test or test(s), any inferential test, or any rule-based test which can be used for model assessment either singly or in combination may be used.

9) Does Test Sample Spectrum Fail within the Range of the Calibration Spectra in the Model In the case of a principal components (or PLS) based analysis, this test refers to an examination of the Euclidean norm calculated from the residual spectrum by summing the squared residuals calculated at each measurement frequency or wavelength. The simulated spectrum only contains eigenspectra upon which the model is based. Therefore spectral features representing chemical species which were not present in the original calibration samples used to generate the model will be contained in the residual spectrum. The Euclidean norm for a test sample containing chemical species which were not included in the calibration samples used to generate the model will be significantly larger than the Euclidean norms calculated for the calibration spectra used to generate the model. As noted in operation [8], any statistic, test or procedure may be used which provides an assessment of whether chemical species are present in the test sample which are not contained in the calibration samples. In particular, pattern recognition techniques and/or comparison to spectra contained in computerized spectral libraries may be used in conjunction with the residual spectrum.

In a preferred way of performing the invention, the magnitude of the Euclidean norm is evaluated to see if the test sample spectrum falls within the range of the calibration sample spectra used to generate the model, i.e. is the Euclidean norm small with respect to the Euclidean norms of the calibration sample spectra calculated in a similar fashion. A small Euclidean norm is taken as indication that no chemical species are present in the test sample that were not present in the calibration samples. If negative (a large Euclidean norm), the sample spectrum is archived and a spot sample collected for further laboratory analysis. This is performed in operation [12]. The sampling system with the analyzer is capable of automatically capturing spot samples upon command by the analyzer control computer.

In the context of this test, chemical species are being thought of as chemical components which are contained in the sample as opposed to external interferences such as water vapor which will also show up here and must be distinguished from chemical components which are present in the sample. This can be done by modelling the measured water vapor spectrum and by orthogonalizing the calibration spectra thereto, as described above in relation to CPSA.

10) Does Test Sample Parameter Estimation involve Interpolation of the Model

If the sample is selected as acceptable in operation [9], it is preferable to examine the validity of the model with respect to accurately estimating properties of this sample. Any method of determining statistical accuracy of parameter estimates or confidence levels is appropriate. A preferred way of achieving this is for the Mahalanobis distance (as defined above in equation (7.1) of the section of this specification describing the development of an empirical model in CPSA) to be used to determine the appropriateness of the model calibration data set for estimating the sample. The Mahalanobis distance is a metric which is larger when a test sample spectrum is farther from the geometric center of the group of spectra used for the model calculation as represented on the hyperspace defined by the principal components or eigenspectra used in the model. Thus, a large value of the Mahalanobis distance indicates that the property estimate is an extrapolation from the range of data covered by the model calibration. This does not necessarily mean that the estimate is wrong, only that the uncertainty in the estimate may be larger (or the confidence level smaller) than desirable and this fact must be communicated in all subsequent uses of the data.

If the estimate is found to be uncertain (large Mahalanobis distance), it is desirable to archive the sample spectrum and capture a spot sample for subsequent laboratory analysis using the computer controlled automatic sampling system [operation 12].

11) Does Test Sample Spectrum Fall in a Polpulated Region of Data in Calibration Model Even though the sample may lie within the data space covered by the model (small value of Mahalanobis distance), the sample may lie in a region in which the number of calibration samples in the model set is sparse. In this case, it is desirable to archive the sample spectrum and capture a spot sample [12] so that the model may be improved. Any standard statistical test of distance may be used in order to make this determination. In particular the inter-sample Mahalanobis distance calculated for each test sample/calibration sample pair may be examined in order to arrive at the decision as to whether or not the samples should be saved. An inter-sample Mahalanobis distance is defined as the sum of the squares of the differences between the scores for the test sample spectrum and those for the calibration sample spectrum, scores being calculated by equation (3.2b) of the section of this specification describing the development of an empirical model in CPSA. A negative response results if all the inter-sample Mahalanobis distances are greater than a predetermined threshold value selected to achieve the desired distribution of calibration sample spectra variability, in which case, it is desirable to archive the sample spectrum and capture a spot sample for subsequent laboratory analysis using the computer controlled automatic sampling system [12].

13) Calculate Parameter and Confidence Interval Estimates

After having performed the statistical tests indicated in operations [9], [10] and [11] and possibly collecting a spot sample as indicated in step [12], the parameters are now estimated from the model. For CPSA, this involves calculating the scores (equation 3.2b) and then estimating the parameters (equations 3.3 to 3.5). The actual numerical calculation performed will depend upon the type of model being used. For the case of a eigenvector-based analysis (such as PCR, PLS), the method is a vector projection method identical to that described above as CPSA.

14) Transmit Estimate(s) to Process Monitor/Control Computer

Having calculated the parameter estimates and the statistical tests, the parameter estimates and estimates of the parameter uncertainties are now available. These may be transmitted to a separate process monitor or control computer normally located in the process control center. The results may be used by operations for many purposes including process control and process diagnostics. Data transmission may be in analog or digital form.

15) Transmit Estimate(s) to Analyzer Workstation

The analyzer is normally operated totally unattended (stand alone). It is desirable for the results of the analysis and statistical tests to be transferred to a workstation which is generally available to analyzer and applications engineers. This is indicated in operation [15]. While the availability of the data on a separate workstation may be convenient, it is not essential to the operation of the analyzer system.

1) Archived Test Spectrum and Lab Data for Model Update Present

In the event that the samples have been captured and spectra archived for subsequent model updating, it is necessary to update the estimation model. This can only be carried out once the results of laboratory analysis are available along with the archived spectrum.

If model updating is not needed, operation continues with [5].

Model Updating

Model updating consists of operations [2], [3], and [4]. Any or all of the operations may be performed on the analyzer computer or may be performed off-line on a separate computer. In the latter case, the results of the updated model must be transferred to the analyzer control computer.

2) Full Model and Regression Calculation Necessary

If the sample which is being included in the model did not result from a negative decision in operation [9], it is not necessary to carry out the calculation which produces the model eigenspectra. This is because operation [9] did not identify the inclusion of additional eigenspectra into the model as being necessary. In this case, only a new regression is required, and the process continues with operation [4].

3) Calculate New Model Using CPSA or Equivalent

The calibration model data base is updated by including the additional spectrum and corresponding laboratory data. The database may be maintained on a separate computer and models developed on that computer. The entire model generation procedure is repeated using the expanded set of data. This, for example, would mean rerunning the CPSA model or whichever numerical methods have been used originally. If this step is performed off-line, then the updated eigenspectra must be transferred to the analyzer computer.

Model updating methods could be developed which would allow an updated model to be estimated without having to rerun the entire model building procedure.

4) Perform New Regression and Update Model Regression Coefficients

A regression is performed using the scores for the updated cailbration set and the laboratory measurements of composition and/or property parameters to obtain regression coefficients which will be used to perform the parameter and confidence interval estimation of operation [13]. The regression step is identical to that described above for CPSA (equations 2.9a and b in the section on the development of an emperical model hereinabove). If this step is performed off-line, then the regression coefficients must be transferred to the analyzer computer.

The steps described above allow the estimation of property and/or composition parameters by performing on-line measurements of the absorbance spectrum of a fluid or gaseous process stream. Mathematical analysis provides high quality estimates of the concentration of chemical components and the concentrations of classes of chemical components. Physical and performance parameters which are directly or indirectly correlated to chemical component concentrations are estimable. Conditions for the measurement of the absorbance spectra are specified so as to provide redundant spectral information thereby allowing the computation of method diagnostic and quality assurance measures.

The steps comprising the methodology are performed in an integrative manner so as to provide continuous estimates for method adjustment, operations diagnosis and automated sample collection. Different aspects of the methodology are set out below in numbered paragraphs (1) to (10).

(1.) Selection of the subset region for the absorbance spectra measurements (1.1) The measurement of the infrared spectrum in the various subregions can be accomplished by the use of different infrared spectrometer equipment. Selection of the appropriate subregion(s) is accomplished by obtaining the spectrum of a representative sample in each of the candidate subregions and selecting the subregion(s) in which absorptions are found which are due directly or indirectly to the chemical constituent(s) of interest. Criteria for selection of the appropriate subregion(s) may be summarized as follows:

The procedure of this paragraph is applicable over a wide range of possible absorption spectrum measurements. No single spectrometer can cover the entire range of applicability. Therefore, it is necessary to select a subset region which matches that which is available in a spectrometer as well as providing significant absorption features for the chemical constituents which are in the sample and which are correlated to the composition and/or property parameter for which a parameter estimate is to be calculated. The criteria for selecting the preferred wavelength subset region include subjective and objective measurements of spectrometer performance, practical sample thickness constraints, achievable sample access, and spectrometer detector choice considerations. The preferred subset region for measuring liquid hydrocarbon process streams is one in which the thickness of the sample is approximately 1 cm. This is achievable in the region from 800 nm to 1600 nm which corresponds to a subset of the near infrared region for which spectrometer equipment which is conveniently adaptable to on-line measurement is currently available. The named region is a further subset of the range which is possible to measure using a single spectrometer. The further restriction on range is preferred in order to include sufficient range to encompass all absorptions having a similar dynamic range in absorbance and restricted to one octave in wavelength.

(2.) Criteria for selection and measurement of samples for the calibration model calculation.
- (2.1) Samples are collected at various times to obtain a set of samples (calibration samples) which are representative of the range of process stream composition variation.
- (2.2) Absorption spectra of the samples may be obtained either on-line during the sample collection procedure or measured separately in a laboratory using the samples collected.
- (2.3) The property and/or composition data for which the calibration model is to be generated are separately measured for the collected samples using standard analytical laboratory techniques.

(3.) Calibration model calculation
- (3.1) The calibration model is obtained using any one of several multivariate methods and the samples obtained are designated calibration samples. Through the application of the method, a set of eigenspectra are obtained which are a specific transformation of the calibration spectra. They are retained for the property/composition estimation step. An important preferred feature of the invention allows for the updating of the predictive model by collecting samples during actual operation. This will permit a better set of samples to be collected as previously unrecognized samples are analyzed and the relevent data entered into the predictive model. Therefore it is not particularly important how the samples are obtained or which model calculation method is used for the initial predictive model. It is preferable that the initial calibration model be developed using the same method which is likely to be used for developing the model from the updated sample set. Methods which can be used for the calibration model calculation are:
  - (b 3.1.1) Constrained Principal Spectra Analysis as described hereinabove is the preferred method.
  - (3.1.2) Principal components regression discussed above is an alternative method.
  - (3.1.3) Partial least squares analysis, which is a specific implementation of the more general principal components regression.
  - (3.1.4) Any specific algorithm which is substantially the same as the above.
  - (3.1.4) A neurological network algorithm, such as back propagation, which is used to produce a parameter estimation model. This technique may have particular advantage for handling non-linear property value estimation.

(4.) Property/composition estimation
- (4.1) Property and/or composition data are estimated according to the following equation as explained above (equation 3.5):

$$y_u = v_u' B$$

(5.) Calibration model validation

Calibration model validation refers to the process of determining whether or not the initial calibration model is correct. Examples of validating the calibration model would be cross-validation or PRESS referred to hereinabove.
- (5.1) Additional samples which are not used in the calibration model calculation (paragraph (3) above) are collected (test set) and measured.
  - (5.1.1) Spectra are measured for these samples either on-line or in a laboratory using the samples which have been collected.
  - (5.1.2) Property and/or composition data are obtained separately from the same standard analytical laboratory analyses referred to in paragraph (2.3) above.
- (5.2) Property and/or composition data are estimated using equations (3.3–3.5) in the description of CPSA hereinabove and validated by comparison to the laboratory obtained property and/or composition data.

(6.) On-line absorption spectrum measurement
- (6.1) Any infrared spectrometer having measurement capabilities in the subset wavelength region determined in paragraph (1) above may be used.
- (6.2) Sampling of the process steam is accomplished either by extracting a sample from the process stream using a slip stream or by inserting an optical probe into the process stream.
  - (6.2.1) Slip stream extraction is used to bring the sample to an absorption spectrum measuring cell. The spectrum of the sample in the cell is measured either by having positioned the cell directly in the light path of the spectrometer or indirectly by coupling the measurement cell to the spectrometer light path using fiber optic technology. Slip stream extraction with indirect fiber optic measurement technology is the preferred on-line measurement method. During the measurement, the sample may either be continuously flowing, in which case the spectrum obtained is a time averaged spectrum, or a valve may be used to stop the flow during the spectral measurement.
  - (6.2.2) Insertion sampling is accomplished by coupling the optical measurement portion of the spectrometer to the sample stream using fiber optic technology.

(7.) Process parameter (on-line property and/or composition) estimation.
- (7.1) Spectra are measured on-line for process stream samples during process operation. Several choices of techniques for performing the spectral measurement are available as described in paragraph (6) immediately above.
- (7.2) Parameter estimation is carried out using the equation in paragraph (4.1) above.

(8.) Calibration model updating
- (8.1) Spot test samples for which the estimated parameter(s) are significantly different from the laboratory measured parameter(s) as determined in paragraphs (9) and (10) below are added to the calibration set and the calibration procedure is repeated starting with paragraph (3) to obtain an updated calibration model as set out in the equation in paragraph (3.1) above.

(8.2) Samples which are measured on-line are compared to the samples used in the calibration model using the methods described in paragraphs (9) and (10) below. Samples for which fall the tests in (9) or (10) are noted and aliquots are collected for laboratory analysis of the property/composition and verification of the spectrum. The on-line measured spectrum and the laboratory determined property/composition data for any such sample is added to the calibration data set and the calibration procedure is repeated starting with paragraph (3) to obtain updated calibration model.

(9.) Diagnostic and quality assurance measures (9.1) Diagnostics are performed by calculating several parameters which measure the similarity of the test sample spectrum to the spectra of samples used in the calibration.

(9.1.1) Vector-based distance and similarity measurements are used to validate the spectral measurements. These include, but are not limited to, (9.1.1.1) Mahalanobis distances and/or Euclidean norms to determine the appropriateness of the calibration set for estimating the sample.

(9.1.1.2) Residual spectrum (the difference between the actual spectrum and the spectrum estimated from the eigenspectra used in the parameter estimation) to determine if unexpected components having significant absorbance are present.

(9.1.1.3) Values of the projection of the spectrum onto any individual eigenspectrum or combination of the eigenspectra to determine if the range of composition observed is included in the calibration set.

(9.1.1.4) Vector estimators of spectrometer system operational conditions (such as wavelength error, radiation source variability, and optical component degradation) which would affect the validity of the parameter estimation or the error associated with the parameter estimated.

(9.1.2) Experienced-based diagnostics commonly obtained by control chart techniques, frequency distribution analysis, or any similar techniques which evaluate the current measurement (either spectral or parameter) in terms of the past experience available either from the calibration sample set or the past on-line sample measurements.

(10.) Process control, optimization and diagnosis (10.1) Parameters are calculated in real-time which are diagnostic of process operation and which can be used for control and/or optimization of the process and/or diagnosis of unusual or unexpected process operation conditions.

(10.1.1) Examples of parameters which are based on the spectral measurement of a single process stream include chemical composition measurements (such as the concentration of individual chemical components as, for example, benzene, toluene, xylene, or the concentration of a class of compounds as, for example, paraffins); physical property measurements (such as density, index of refraction, hardness, viscosity, flash point, pour point, vapor pressure); performance property measurement (such as octane number, cetane number, combustibility); and perception (such as smell/odor, color).

(10.1.2) Parameters which are based on the spectral measurements of two or more streams sampled at different points in the process, thereby measuring the difference (delta) attributable to the process included between the sampling points along with any delayed effect of process between to the sampling points.

(10.1.3) Parameters which are based on one or more spectral measurements along with other process operational measurements (such as temperatures, pressures, flow rates) are used to calculate a multi-parameter (multivariate) process model.

(10.2) Real-time parameters as described in paragraph (10.1) can be used for:

(10.2.1) Process operation monitoring.

(10.2.2) Process control either as part of a feedback or a feedforward control strategy.

(10.2.3) Process diagnosis and/or optimization by observing process response and trends.

It will be appreciated that many modifications to or additions in the inventive method and apparatus disclosed herein are possible without departing from the spirit and scope of the invention or defined by the appended claims. All such modifications and additions will be obvious to the skilled addressee, are contemplated by the disclosure of the present invention, and will not be further described herein.

The concepts and mathematical techniques disclosed in this patent specification are relatively complex. Although the invention has been fully described in the foregoing pages, there is set out hereinafter, under the heading "Appendix," a detailed description of the mathematical techniques used, starting from first principles. This Appendix forms part of the disclosure of the present specification.

APPENDIX 1.0 Definition of Mathematical Terms, Symbols and Equations:

1.1 Scalars:

Variables representing scalar quanitites will be designated by lowercase, normal typeface letters, e.g. x or y. Scalar quanities are real numbers. Examples would include but not be limited to the concentration of a single component in a single sample, the value of a single property for a single sample, the absorbance at a single frequency for a single sample.

1.2 Vectors:

Vectors will be represented as lowercase, boldface letters. Vectors are a one dimensional array of scalar values. Two types of vectors will be distinguished.

$$v = \begin{pmatrix} v_1 \\ v_2 \\ v_3 \\ v_4 \\ v_5 \\ v_6 \\ v_7 \\ v_8 \\ v_9 \end{pmatrix} \text{ is an example of a column vector of dimension 9.}$$

The corresponding row vector, $v^t = (v_1\ v_2\ v_3\ v_4\ v_5\ v_6\ v_7\ v_8\ v_9)$ is also of dimension 9. The superscript $t$ indicates that the row vector is the transpose of the corresponding column vector.

Normal face, lowercase letters with subscripts will be used to refer to the individual elements of the vector, e.g $v_1$, $v_2$, $v_3$, etc., which are scalar quanities. The subscripts $1,2,3$, etc. indicate the position of the quantity in the vector. The expression $v_i$ will be used to represent a general position i in the vector. Bold face, lowercase letters with subscripts will be used to represent one of a set of vectors, i.e. $\mathbf{v}_1$, $\mathbf{v}_2$, ... $\mathbf{v}_n$ would be a set of n vectors.

1.2.1 Product of a Scalar Times a Vector:

If $v = \begin{pmatrix} v_1 \\ v_2 \\ v_3 \\ v_4 \\ v_5 \\ v_6 \\ v_7 \\ v_8 \\ v_9 \end{pmatrix}$, then the multiplication of $v$ by a scalar $a$ is $va = \begin{pmatrix} av_1 \\ av_2 \\ av_3 \\ av_4 \\ av_5 \\ av_6 \\ av_7 \\ av_8 \\ av_9 \end{pmatrix}$ If $v^t = (v_1\ v_2\ v_3\ v_4\ v_5\ v_6\ v_8\ v_9)$ then $av^t = (av_1\ av_2\ av_3\ av_4\ av_5\ av_6\ av_7\ av_8\ av_9)$

1.2.2 Dot Product of two vectors:

The dot product of a column and a row vector is a scalar quanity. The dot product is defined only if the vectors are of the same dimension. The dot product is the sum of the products of the individual elements of the two vectors, i.e.

$u^t v = (u_1\ u_2\ u_3\ u_4\ u_5\ u_6\ u_7) \begin{pmatrix} v_1 \\ v_2 \\ v_3 \\ v_4 \\ v_5 \\ v_6 \\ v_7 \end{pmatrix} =$ $u_1 v_1 + u_2 v_2 + u_3 v_3 + u_4 v_4 + u_5 v_5 + u_6 v_6 + u_7 v_7$ Two vectors will be referred to as being orthogonal if their dot product is equal to zero. If a vector z is orthogonal to vectors u and v, it is orthogonal to any linear combination of u and v, i.e.

if $z^t u = z^t v = 0$ and $y = ua + vb$ for any scalar coefficients a and b then $z^t y = z^t ua + z^t vb = 0a + 0b = 0$.

1.2.3 Length of a Vector:

The length of a vector is the square root of the dot product of the vector with its transpose, and will be designated by $\|v\|$, i.e.

$$\|v\| = \|v^t\| = (v^t v)^{0.5}$$

A vector will be referred to as normal, unit or normalized if the length of the vector is equal to one. A zero vector refers to a vector of zero length, i.e. one whose elements are all zero.

1.2.4 An Orthonormal Set of Vectors:

A set of vectors $\mathbf{u}_1$, $\mathbf{u}_2$, ... $\mathbf{u}_n$, form an orthonormal set if the dot products $u_i^t u_i = 1$ and $u_i^t u_j = 0$ for $i$ not equal to $j$ where $i$ and $j$ run from $1$ to $n$. The individual vectors are normalized, and the dot products between any two different vectors is equal to zero.

1.2.5 Orthogonalization and Normalization of Vectors:

Given a vector u of length $\|u\|$, it is possible to define a new, normal vector u' as $u' = u / \|u\|$. u' is obtained from u by dividing each of the elements by the length of the vector. This procedure is referred to as normalization of the vector.

If u is a normal vector, and v is a vector such that the dot product $u^t v = d$, the vector $z = v - du$ is orthogonal to u, i.e. $u^t z = u^t v - du^t u = d - d = 0$. The procedure for calculating z is referred to as orthogonalization of the vectors.

Given a set of n vectors, $x_1$, $x_2$, ... $x_n$, it is possible to derive a new set of n vectors, $u_1$, $u_2$, ... $u_n$, that form an orthonormal set. This procedure which is referred to as Gram-Schmidt Orthogonalization involves the following steps:

[1] chosing an initial vector, $x_1$, and normalizing it to produce $u_1$;

[2] choosing a second vector, $x_2$, orthogonalizing it to $u_1$ normalizing the resultant vector to produce $u_2$;

[3] choosing a third vector, $x_3$, orthogonalizing it to both $u_1$ and $u_2$, and normalizing the result to produce $u_3$;

[4] continuing the process of choosing vectors $x_i$, orthogonalizing them to the vectors $u_1$, $u_2$, ... $u_{i-1}$ which were already calculated, and normaling the resultant vectors to produce new $u_i$ until all vectors have been processed.

1.3 Matrices:

A matrix is a two dimensional array of scalar values. Matrices will be designated as uppercase, boldfaced letters. For example, $X = \begin{pmatrix} x_{11}\ x_{12}\ x_{13}\ x_{14} \\ x_{21}\ x_{22}\ x_{23}\ x_{24} \\ x_{31}\ x_{32}\ x_{33}\ x_{34} \\ x_{41}\ x_{42}\ x_{43}\ x_{44} \\ x_{51}\ x_{52}\ x_{53}\ x_{54} \\ x_{61}\ x_{62}\ x_{63}\ x_{64} \\ x_{71}\ x_{72}\ x_{73}\ x_{74} \\ x_{81}\ x_{82}\ x_{83}\ x_{84} \\ x_{91}\ x_{92}\ x_{93}\ x_{94} \end{pmatrix}$ is a 9 by 4 matrix.

The general element of the matrix X, $x_{ij}$, indicates the value in the $i^{th}$ row and the $j^{th}$ column. The dimensions of a matrix, i.e. the numbers of rows and columns, will be indicated as italicized, lowercase letters, i.e. a matrix X of dimension f by n where in the above example f is 9, and n is 4. The individual columns of a matrix are column vectors, e.g. the vector $x_1$ would be the vector containing the same elements as the first column of the matrix X. The individual rows of a matrix are row vectors, e.g. the vector $x_i^t$ is the $i^{th}$ row of the matrix X.

1.3.1 Matrix Transpose:

The transpose of a matrix X is obtained by interchanging the rows and columns, and will be designated by $X^t$. For example, $$\text{if } X = \begin{pmatrix} x_{11} & x_{12} & x_{13} & x_{14} \\ x_{21} & x_{22} & x_{23} & x_{24} \\ x_{31} & x_{32} & x_{33} & x_{34} \\ x_{41} & x_{42} & x_{43} & x_{44} \\ x_{51} & x_{52} & x_{53} & x_{54} \\ x_{61} & x_{62} & x_{63} & x_{64} \\ x_{71} & x_{72} & x_{73} & x_{74} \\ x_{81} & x_{82} & x_{83} & x_{84} \\ x_{91} & x_{92} & x_{93} & x_{94} \end{pmatrix}$$

$$\text{then } X^t = \begin{pmatrix} x_{11} & x_{21} & x_{31} & x_{41} & x_{51} & x_{61} & x_{71} & x_{81} & x_{91} \\ x_{12} & x_{22} & x_{32} & x_{42} & x_{52} & x_{62} & x_{72} & x_{82} & x_{92} \\ x_{13} & x_{23} & x_{33} & x_{43} & x_{53} & x_{63} & x_{73} & x_{83} & x_{93} \\ x_{14} & x_{24} & x_{34} & x_{44} & x_{54} & x_{64} & x_{74} & x_{84} & x_{94} \end{pmatrix}$$

If the matrix X is of dimension f by n, then the matrix $X^t$ is of dimension n by f.

1.3.2 Matrix Multiplication:

If U is a matrix of dimension f by k, and V is a matrix of dimension k by n. then the product matrix Z=UV is a matrix of dimension f by n. The $z_{ij}$ element of Z is calculated by taking the dot product of the $i^{th}$ row vector $u_i^t$ from U and the $j^{th}$ column vector $v_j$ for V.

$$\text{If } U = \begin{pmatrix} u_{11} & u_{12} \\ u_{21} & u_{22} \\ u_{31} & u_{32} \\ u_{41} & u_{42} \end{pmatrix} \text{ and } V = \begin{pmatrix} v_{11} & v_{12} & v_{13} \\ v_{21} & v_{22} & v_{23} \end{pmatrix}$$

then $Z =$ $$UV = \begin{pmatrix} u_{11}v_{11} + u_{12}v_{21} & u_{11}v_{12} + u_{12}v_{22} & u_{11}v_{13} + u_{12}v_{23} \\ u_{21}v_{11} + u_{22}v_{21} & u_{21}v_{12} + u_{22}v_{22} & u_{21}v_{13} + u_{22}v_{23} \\ u_{31}v_{11} + u_{32}v_{21} & u_{31}v_{12} + u_{32}v_{22} & u_{31}v_{13} + u_{32}v_{23} \\ u_{41}v_{11} + u_{42}v_{21} & u_{41}v_{12} + u_{42}v_{22} & u_{41}v_{13} + u_{42}v_{23} \end{pmatrix}$$

The product is only defined if the inner dimensions of the two matrices, e.g k in this example, are the same. The vectors formed by the columns of the product matrix Z are linear combinations of the column vectors of U, i.e.

$$z_1 = \begin{pmatrix} u_{11}v_{11} + u_{12}v_{21} \\ u_{21}v_{11} + u_{22}v_{21} \\ u_{31}v_{11} + u_{32}v_{21} \\ u_{41}v_{11} + u_{42}v_{21} \end{pmatrix} = \begin{pmatrix} u_{11} \\ u_{21} \\ u_{31} \\ u_{41} \end{pmatrix} v_{11} +$$

$$\begin{pmatrix} u_{12} \\ u_{22} \\ u_{32} \\ u_{42} \end{pmatrix} v_{21} = u_1 v_{11} + u_2 v_{21}$$

The product of more that two matrices, e.g. ABC, is obtained by taking the products of the matrices two at a time, i.e. the product of AB times C, or A times the product of BC.

The transpose of a product of two matrices is the product of the transposes in opposite order, i.e.

$$(AB)^t = B^t A^t.$$

1.3.3 Products of Vectors and Matrices:

The product of a row vector $u^t$ of dimension k by a matrix V of dimension k by n is a column vector z of dimension n, i.e.

$$\text{If } u^t = (u_1 \ u_2) \text{ and } V = \begin{pmatrix} v_{11} & v_{12} & v_{13} \\ v_{21} & v_{22} & v_{23} \end{pmatrix}$$

then $z = (z_1 \ z_2 \ z_3) = u^t V = (u_1 v_{11} + u_2 v_{21} \ u_1 v_{12} + u_2 v_{22} \ u_1 v_{13} + u_2 v_{23})$ The individual elements of z, $z_i$, is calculated as the dot product of $u^t$ with the individual column vectors of V, $v_i$. The product of a matrix U of dimension f by k with a column vector v of dimension k, is a column vector z which is calculated by taking the dot product of the row vectors of U, $u_i^t$, with v.

$$\text{If } U = \begin{pmatrix} u_{11} & u_{12} \\ u_{21} & u_{22} \\ u_{31} & u_{32} \\ u_{41} & u_{42} \end{pmatrix} \text{ and } v = \begin{pmatrix} v_1 \\ v_2 \end{pmatrix}$$

$$\text{then } z = \begin{pmatrix} z_1 \\ z_2 \\ z_3 \\ z_4 \end{pmatrix} = Uv = \begin{pmatrix} u_{11}v_1 + u_{12}v_2 \\ u_{21}v_1 + u_{22}v_2 \\ u_{31}v_1 + u_{32}v_2 \\ u_{41}v_1 + u_{42}v_2 \end{pmatrix}$$

1.3.4 Square, Diagonal and Unit and Unitary Matrices:

A square matrix is a matrix whose two dimensions are equal. The diagonal elements of a matrix are the elements $x_{ii}$. The off-diagonal elements of a matrix are the elements $x_{ij}$ for which $i \neq j$. A diagonal matrix is a matrix for which the off-diagonal elements are zero. A unit matrix, wherein designated as I, is a square, diagonal matrix where all the diagonal elements are equal to one. The product of a matrix with an unit matrix is itself, i.e. AI=A. A unitary matrix is a square matrix U for which $$U^tU = UU^t = I.$$

The column and row vectors of a unitary matrix are orthonormal sets of vectors.

1.3.5 Matrix Inverse:

For a square matrix A of dimension n by n, the inverse of A, $A^{-1}$, is the matrix for which $$AA^{-1} = A^{-1}A = I.$$

The inverse of A may not exist if the rank of A (see section 1.3.6) is less than n. Various computer algorithms are available for calculating the inverse of a square matrix (1).

A non-square matrix U of dimension f by n may have a right inverse, $$UU^{-1} = I \text{ if } f < n$$

or it may have a left inverse, $$U^{-1}U = I \text{ if } f > n.$$

If $f < n$, and $U^{-1}U = I$ then $U^{-1} = U^t(UU^t)^{-1}$.

If $f > n$, and $UU^{-1} = I$ then $U^{-1} = (U^tU)^{-1}U^t$.

1.3.6 Eigenvalues and Eigenvectors:

For a square matrix A of dimension n by n, the equation $$Av = v\lambda_i$$

is called the eigenvalue equation for A. The eigenvalues of A, $\lambda_i$, are the scalars for which the equation possesses nonzero solutions in v. The corresponding nonzero vectors $v_i$ are the eigenvectors of A. The eigenvectors of A form an orthonormal set of vectors. The eigenvalue equation may also be written as $$AV = V\Lambda$$

or as $$V^tAV = \Lambda$$

where $\Lambda$ is a diagonal matrix containing the eigenvalues $\lambda_i$, and V is the unitary matrix whose columns are the individual eigenvectors. The eigenvalues of A can be obtained by solving the equation $$det(A = \Lambda I) = 0$$

where det indicates the determinant of the matrix. Various computer algorithms are availabe for solving for the eigenvalues and eigenvectors of a square matrix (1).

The rank of a matrix A is equal to the number of nonzero eigenvalues of A. The rank of a square matrix A of dimension n by n is at most n. If the rank of A is less than n, then A is singular and cannot be inverted.

1.3.7 Singular Value Decomposition of a Matrix:

For a non-square matrix X of dimension f by n, the singular value decomposition of X is given by $$X = U\Sigma V^t$$

If $f > n$, then U (dimension f by n), $\Sigma$ (dimension n by n), and V (dimension n by n) matrices have the following properties:

$$U^tU = I$$

$\Sigma$ is a diagonal matrix $$V^tV = VV^t = I$$

If $f < n$, then U (dimension f by f), $\Sigma$ (dimension f by f), and V (dimension n by f) matrices have the following properties:

$$U^tU = UU^t = I$$

$\Sigma$ is a diagonal matrix $$V^tV = I$$

The vectors which make up the columns of U are refered to as the left eigenvectors of X, and the vectors which make up the columns of V are referred to as the right eigenvectors of X. The diagonal element of $\Sigma$, $\sigma_{ii}$, are referred to as the singular values of X, and are in the order $\sigma_{11} > \sigma_{22} > \sigma_{33} > \ldots \sigma_{kk}$ where $k$ is the smaller of f or n.

The singular value decomposition of $X^t$ is $V\Sigma U^t$.

The singular value decomposition is related to the eigenvalue analysis in the following manner. The eigenvalue equation for the square matrix $X^tX$ can be written as $$X^tXV = V\Lambda.$$

By substituting the singular value decomposition for X and $X^t$ we obtain $$X^tXV = V\Sigma^tU^tU\Sigma V^tV = V\Lambda.$$

Using the fact that $U^tU = I$ and $V^tV = I$ and that $\Sigma^t = \Sigma$ we obtain $$X^tXV = V\Sigma^2$$

where $\Sigma^2 = \Sigma\Sigma$. From this it can be seen that V is the matrix of eigenvectors for the $X^tX$ matrix, and that $$\Sigma^2 = \Lambda$$

i.e. the singular values of X are the square roots of the eigenvalues of $X^tX$. Similarly, for the matrix $XX^t$ $$XX^tU = U\Sigma V^tV\Sigma U^tU = U\Sigma^2 = U\Lambda$$

U is the matrix of eigenvectors of the $XX^t$ matrix. Note that if $f \geq n$, $X^tX$ and $XX^t$ have at most n nonzero eigenvalues. Similarly if $f \leq n$, $X^tX$ and $XX^t$ have at most f nonzero eigenvalues.

If X is of dimension f by n, then the inverse of X is given by $V\Sigma^{-1}U^t$, i.e.

$$X^{-1}X = V\Sigma^{-1}U^tX = V\Sigma^{-1}U^tU\Sigma V^t = VV^t$$

$$XX^{-1} = XV\Sigma^{-1}U^t = U\Sigma V^tV\Sigma^{-1}U^t = UU^t$$

where $\Sigma^{-1}$ is a diagonal matrix containing $1/\sigma_i$ on the diagonal. Similarly, the inverse of $X^t$ is given by $U\Sigma^{-1}V^t$, i.e.

$$X^t(X^t)^{-1} = X^tU\Sigma^{-1}V^t = V\Sigma U^tU\Sigma^{-1}V^t = VV^t$$

$$(X^t)^{-1}X^t = U\Sigma^{-1}V^tX^t = U\Sigma^{-1}V^tV\Sigma U^t = UU^t$$

If X if square and of rank $k = f = n$, then $$VV^t = I \text{ and } UU^t = I$$

In this case, X and $X^t$ both have right and left inverses.

If $f > n$, $UU^t$ is not an identity matrix, and the expressions for the right inverse of X and for the left inverse of $X^t$ are only approximate. Similarly, if $f < n$, $VV^t$ is not an identity matrix, and the expressions given for the left inverse of X and for the right inverse of $X^t$ are only approximate.

If $\Sigma$ contains k nonzero singular values, then $$X = U\Sigma V^t = U'\Sigma' V'^t$$

where $\Sigma'$ is the k by k matrix containing the nonzero singular values, and $U'$ and $V'$ are the f by k and n by k matrices obtained from U and V by eliminating the columns which correspond to the singular values that are zero. Similarly, $$X^t = V'\Sigma' U'^t$$

$$X^{-1} = V'\Sigma'^{-1} U'^t$$

$$(X^t)^{-1} = U'\Sigma'^{-1} V'^t$$

Similarly, if the k+1 through n singular values of X are close to zero, these singular values and the corresponding columns of U and V may be eliminated to provide an approximation to the X matrix $X \simeq U'\Sigma'V'^t$. Approximations for $X^t$ and for the inverses of X and $X^t$ are obtained similarly.

In developing regression models, it is generally assumed that small singular values correspond to random errors in the X data, and that removal of these values improves the stability and robustness of the regression models. To simplify the notation in the discussion below, the ' will be dropped, and the symbols U, $\Sigma$, and V will represent the f by k, k by k, and n by k matrices obtained after eliminating the singular values that are at, or close to zero.

The matrix U is can be calculated as $$U = XV\Sigma^{-1}$$

which implies that the column vectors in U are linear combinations of the column vectors in X.

It should be noted that in some versions of Principal Component Analysis, the X matrix is decomposed into only two matrices $$X = LV$$

The L matrix is the product of the U and $\Sigma$ matrices, such that $$L^t L = \Lambda$$

1.4.1 Multiple Linear Regression, Least Squares Regression:

If y is a column vector of length n, and X is a matrix of dimension f by n, then the matrix equation $$y = X^t p + e$$

is a linear regression equation relating the dependent variable y to the independent variables X. p is a column vector of length f containing the regression coefficients, and e is the vector containing the residuals for the regression model. A least square regression is one that minimizes $e^t e$, i.e. the sum of the square of the residuals.

1.4.2 Solution for $f \leq n$:

If X if f by n, y is of dimension n, and $f \leq n$, then the solution to the regression equation that minimizes $\|e\|$ is obtained by multiplying both sides of the equation in 1.4.1 by the left inverse of $X^t$, i.e.

$$y = X^t p + e \rightarrow (XX^t)^{-1} X y = (XX^t)^{-1} XX^t p + (XX^t)^{-1} X e = p + (XX^t)^{-1} X e$$

The quanity $(XX^t)^{-1} Xy$ is the least square estimate of p, and is designated p.

$$p = (XX^t)^{-1} Xy$$

The regression vector p is a linear combination of the column vectors in X. The estimates of y, i.e. $\hat{y}$, are given by $$\hat{y} = X^t p = X^t (XX^t)^{-1} Xy$$

The residuals for the model are $$e = y - \hat{y}$$

The Standard Error of Estimate (SEE) for the model is $$SEE = \sqrt{e^t e / (n - f)}$$

The regression model may be used to estimate the scalar value $y_u$ corresponding to a new vector of independent variables $x_u$ $$y_u = x_u^t p = x_u^t (XX^t)^{-1} Xy$$

Based on the model, the probability is a that the true value $y_u$ lies in range $$y_u - t \cdot SEE \cdot \sqrt{1 + d^2} \leq y_u \leq y_u + t \cdot SEE \cdot \sqrt{1 + d^2}$$

where t is the student's t distribution value for probability a and n−f degrees of freedom, and $d^2$ is given by $$d^2 = x_u^t (XX^t)^{-1} x_u$$

An equivalent solution for this case can be obtained using the singular value decomposition of $X^t$, i.e.

$$U\Sigma^{-1} V^t y = p + U\Sigma^{-1} V^t e$$

The solution can be seen to be equivalent since $$(XX^t)^{-1} X = (U\Sigma V^t V\Sigma U^t)^{-1} U\Sigma V^t = (U\Sigma^{-2} U^t) U\Sigma V^t = U\Sigma^{-1} V^t.$$

1.4.3 Solutions for $f > n$:

If $f > n$, the matrix $X^t$ does not possess a left inverse since $XX^t$ is a f by f matrix of rank at most n. In this case, an approximate solution to the regression equations can be derived using methods such as Principal Components Regression or Partial Least Squares.

1.4.3.1 Principal Components Regression:

Principal Components Regression (PCR) uses the singular value decomposition of the $X^t$ matrix to approximate a solution to the regression equation, i.e. the equation $$y = X^t p + e$$

is solved as $$U\Sigma^{-1}V^t y = U\Sigma^{-1}V^t X^t p + U\Sigma^{-1}V^t e = p + U\Sigma^{-1}V^t e$$

where U is of dimension f by k, $\Sigma$ and $\Sigma^{-1}$ are k by k, and V is n by k. The estimate of the regression vector is $$p = U\Sigma^{-1}V^t y = X V \Sigma^{-2} V^t y$$

p is a linear combination of the column vectors of both U and X. The estimate of y is $$y = X^t p = X^t U\Sigma^{-1}V^t y = V\Sigma U^t U\Sigma^{-1}V^t y = V V^t y.$$

The residuals from the model are $$e = y - \hat{y} = y - V V^t y$$

The Standard Error of Estimate is $$SEE = \sqrt{e^t e / (n - k)}$$

For a new vector of independent variables $x_u$, the scalar estimate $y_u$ is obtained as $$y_u = x_u^t p = x_u^t U\Sigma^{-1}V^t y = v_u^t V^t y \text{ where } v_u^t = x_u^t U\Sigma^{-1}$$

Based on the model, the probability is a that the true value $y_u$ lies in range $$y_u - t \cdot SEE \cdot \sqrt{1 + d^2} \leq y_u \leq y_u + t \cdot SEE \cdot \sqrt{1 + d^2}$$

where t is the student's t distribution value for probability a and $n - k$ degrees of freedom, and $d^2$ is given by $$d^2 = x_u^t (XX^t)^{-1} x_u = v_u^t \Sigma U^t (U\Sigma V^t V\Sigma U^t)^{-1} U\Sigma v_u = v_u^t \Sigma U^t (U\Lambda U^t)^{-1} U\Sigma v_u$$

$$d^2 = v_u^t \Sigma U^t U\Lambda^{-1} U^t U\Sigma v_u = v_u^t \Sigma \Lambda^{-1} \Sigma v_u = v_u^t v_u$$

decomposing the X matrix into $U\Sigma V^t$, and regressing y versus V, i.e.

$$X = U\Sigma V^t \text{ and } y = Vb + e$$

where b is a vector of regression coefficients. The solution is $$V^t y = V^t V b + V^t e = b + V^t e.$$

The estimate of the coefficients is $$b = (V^t V)^{-1} V^t y = V^t y$$

The estimate y is $$\hat{y} = Vb = V V^t y$$

which is the same as obtained above. For a new vector of independent variables $x_u$, $v_u^t$ is calculated as $$v_u^t = x_u^t U\Sigma^{-1}$$

and the estimation of the scalar $y_u$ is $$y_u = v_u^t b = v_u^t V^t y = x_u^t U\Sigma^{-1} V^t y = x_u^t p$$

which is again the same as that obtained above. The residuals, SEE and $d^2$ are also the same as that shown for the first PCR method.

1.4.3.2 Step-wise and PRESS Regression:

An advantage to using the alternative method for calculating a Principal Components Regression is that the coefficients $b_i$ which are small and statistically equivalent to zero may be detected and removed from the model (i.e. set to zero) prior to estimation of y, thereby reducing the variation in the estimate. The coefficients which can be set to zero may be determined using, for example, a step-wise regression algorithm (2).

In the first step of a possible step-wise regression calculation, a series of equations of the form $$y = v_i b_i + e_i$$

where $v_i$ are the column vectors of the V matrix. The scalar coefficient $b_i$ $$b_i = v_i^t y$$

that produces the minimal sum of squares of residuals, $e_i^t e_i$, is initially chosen. If $b_k$ is the coefficient that produced the minimum sum of square of resiudal, the the 1st and $k^{th}$ columns of V are interchanged. The one variable model at the end of the first step is then $$y = v_1 b_1 + e_1$$

In the second step, a series of equations of the form $$y = v_1 b_1 + v_i b_i + e_i$$

are then constructed for each column vector $v_i$ where $i$ is not equal to 1. The equations are solved for the various combinations of $b_1$ and $b_i$, and the residual sum of squares $e_i^t e_i$ is calculated for all the combinations. If $b_k$ is the coefficient that produced the minimum residual sum of squares, then $e_k^t e_k$ is compared to $e_1^t e_1$ via an F-test (3). If the inclusion of $b_k$ produces a statistically significant improvement in the sum of the squares of the residuals, the $2^{nd}$ and $k^{th}$ columns of V are interchanged. At the end of the second step, two variable model then becomes $$y = v_1 b_1 + v_2 b_2 + e_2$$

If no coefficient $b_k$ produces a statistically significant decrease in the sum of squares of the residuals, then the one variable model previously determined is the final model, and the step-wise procedure is completed.

If, at the end of the second step, a two variable model is found, a series of models of the form $$y = v_1 b_1 + v_2 b_2 + v_i b_i + e_i$$

are tested for all i not equal to 1 or 2. If, in this third step, a coefficient $b_k$ is found such that $e_k^t e_k$ is less than $e_2^t e_2$ by a statistically signficant amount, then the $3^{rd}$ and $k^{th}$ columns of V are interchanged, and the three variable model becomes $$y = v_1 b_1 + v_2 b_2 + v_3 b_3 + e_3$$

At this point, models of the form $$y = v_1 b_1 + v_3 b_3 + e_{13}$$

$$y = v_2 b_2 + v_3 b_3 + e_{23}$$

are formed to test for deletion of variables from the model. If $e_{13}'e_{13}$ is less than $e_3'e_e$ by a statistically significant amount, then the $2^{nd}$ and $3^{rd}$ column vectors of V are interchanged and a new two variable model is obtained. Similarly, if $e_{23}'e_{23}$ is less than $e_3'e_3$ then the $1^{st}$ and $3^{rd}$ columns of V are interchanged to produce a new two variable model. At this point procedure then repeats the third step of testing possible three variable models. If a new three variable model which produces a statistically significant reduction in the sum of the squares of the resiudals is found, tests are again conducted on deleting one of the three variables. If no new three variable model is found, the two variable model is the final model, and the step-wise procedure is finished. If a three variable model is generated from which no variables can be deleted, the third step is completed, and the procedure continues with a fourth step in which four variable models are tested. If a four variable model is generated from which no variables can be deleted, a fifth step is conducted to test five variable models. This step-wise procedure continues until no varibles can be added or deleted to produce a statistically significant change in the residuals, or until all the k variables are included in the model, whichever comes first. Algorithms for efficiently conducting this step-wise procedure have been published(2).

An alternative to the step-wise regression calculation is a step-wise Predictive Residual Sum of Squares (PRESS) algorithm. This algorithm can also be used to determine which coefficients to include in the model. For PRESS, a model is built setting the $i^{th}$ dependent variable $y_i$, and the corresponding row vector, $v_i^t$, to zero.

The model has the form $$(y - y_i) = (V - v_i^t) b(i) + e$$

where $(y - y_i)$ is the vector obtained form y by setting $y_i$ to zero, and $(V - v_i^t)$ is the matrix obtained from V by setting the $i^{th}$ row to zero. For example, $$\text{if } y = \begin{pmatrix} y_1 \\ y_2 \\ y_3 \\ y_4 \end{pmatrix} \text{ and } V = \begin{pmatrix} v_{11} & v_{12} \\ v_{21} & v_{22} \\ v_{31} & v_{32} \\ v_{41} & v_{42} \end{pmatrix}$$

$$\text{then } (y - y_2) = \begin{pmatrix} y_1 \\ 0 \\ y_3 \\ y_4 \end{pmatrix} \text{ and } (V - v_2^t) = \begin{pmatrix} v_{11} & v_{12} \\ 0 & 0 \\ v_{31} & v_{32} \\ v_{41} & v_{42} \end{pmatrix}$$

The estimate of the coefficient vector for this model is $$b(i) = [(V - v_i^t)^t (V - v_i^t)]^{-1} (V - v_i^t)(y - y_i)$$

$$b(i) = [(V^t V)^{-1} + (V^t V)^{-1} v_i (1 - v_i^t (V^t V)^{-1} v_i)^{-1} v_i^t (V^t V)^{-1}] (V - v_i^t)(y - y_i)$$

The estimate of $y_i$ based on this model, y(i), is then given by $$y(i) = v_i^t b = v_i^t [(V^t V)^{-1} + (V^t V)^{-1} v_i (1 - v_i^t (V^t V)^{-1} v_i^t (V^t V)^{-1}] (V - v_i^t)(y - y_i)$$

The estimate may be simplified to yield $$y(i) = (1 - q_i)^{-1} y_i - q_i (1 - q_i)^{-1} y_i$$

where $$q_i = v_i^t (V^t V)^{-1} v_i$$

and $y_i$ is the estimate based on a model including all the variables $$y_i = v_i^t (V^t V)^{-1} V^t y.$$

The residual for the $i^{th}$ dependent variable is then $$y_i - y(i) = (1 - q_i)^{-1} (y_i - y_i)$$

The PRESS statistic is the sum of these residuals over all i=1 to n.

The first step in the PRESS algorithm, n by 1 matrices $V_j$ are formed from the k columns of V. The n values of $q_i$ are calculated as $$q_i = v_i^t (V_j^t V_j)^{-1} v_i$$

and the residuals and PRESS values are calculated using the equations above. If $V_k$ is the matrix which yields the minimum value of PRESS, then the $1^{st}$ and the $k^{th}$ columns of V are interchanged.

In the second step, n by 2 matrices $V_j$ are formed using the 1st and $j^{th}$ ($j \neq 1$) columns of V. The $q_i$, residuals and PRESS values are again calculated. If no matrix $V_k$ yields a PRESS value less than that calculated in step 1, then the one variable model from the first step is the final model and the procedure is finished. If a $V_k$ is found that yields a smaller PRESS value, then the $2^{nd}$ and $k^{th}$ columns of V are interchanged, and a third step is conducted.

The third step involves forming n by 3 matrices $V_j$ using the $1^{st}$, $2^{nd}$ and $j^{th}$ ($j \neq 1,2$) columns of V. $q_i$, residuals, and PRESS values are again calculated. If no matrix $V_k$ yields a PRESS value lower than that calculated in step 2, then the two variable is the final model, and the procedure is finished. Otherwise, the $3^{rd}$ and $k^{th}$ columns of V are interchanged and the procedure continues.

The $m^{th}$ step in the n by m matrices $V_j$ using the $1^{st}$, $2^{nd}$, ... (m−1) and $j^{th}$ ($j \neq 1,2, \ldots, m-1$) columns of V, calculating $q_i$, the residuals and PRESS. If no matrices yield PRESS values less than that from the previous step, the model having m−1 variables is the final model, and the procedure is finished. If a matrix $V_k$ yields a PRESS value that is less than that calculated in the previous step, the $m^{th}$ and $k^{th}$ columns of V are interchanged, and another step is initiated.

A computer algorithm for efficiently doing a step-wise PRESS selection of variables was given by Allen (4).

Since the models calculated using these step-wise procedures may contain k' < k nonzero coefficients, the degrees of freedom used in the calculation of SEE becomes n−k', i.e.

$$SEE = \sqrt{e'e/(n - k')}$$

where e are the residuals for the final model. Based on the model, the probability is a that the true value $y_u$ lies in range $$y_u - t' \cdot SEE \cdot \sqrt{1 + d^2} \leq y_u \leq y_u + t' \cdot SEE \cdot \sqrt{1 + d^2}$$

where t' is the student's t distribution value for probability a and n−k' degrees of freedom, and $d^2$ is given by $$d^2 = v'_u t v'_u$$

where v' is a vector of dimension k' obtained from v by deleting the elements whose corresponding coeffiecients were set to zero during the regression.

1.4.3.2 Partial Least Squares Regression:

Partial Least Squares (PLS) Regression is similar to Principal Components Regression in that the f by n matrix X is decomposed into the product of orthogonal matrices, i.e.

$$X = LS^t$$

where S is a n by k matrix, L is a f by k matrix. The matrices L and S have the following properties:

$$L^t L = I$$

$$S^t S = D$$

where D is a diaginal matrix. The dependent variable is regressed against one of these matrices, i.e.

$$y = Sb + e$$

PLS differs from PCR in the way that the matrices are determined. A step in the PLS regression proceeds by the following 10 calculations:

[1] A vector $u_1$ of dimension n is set equal to y, $u_1 = y$

[2] A weighting vector of dimension f is then calculated as $$w'_1 = Xu_1$$

[3] The weighting vector is normalized $$w_1 = w'_1 / \|w'_1\|$$

[4] A scores vector $s'_1$ of dimension n is calculated as $$s'_1 = X^t w_1$$

[5] A loadings vector of dimension f is calculated as $$l'_1 = Xs'_1 / \|s'_1\|$$

[6] The loadings vector is normalized as $$l_1 = l'_1 / \|l_1\|$$

[7] The scores vector is scaled as $$s_1 = s'_1 \|l_1\|$$

[8] The residuals for the X matrix are calculated as $$E_1 = X - ls^t$$

[9] A estimate of the coefficient $b_1$ is calculated from the relationship $$y = s_1 b_1 + e$$

$$b_1 = (s_1^t s_1)^{-1} s_1^t y$$

[10] The residuals from the y vector are calculated as $$e_1 = y - s_1 b_1.$$

At this point, the a new vector $u_2$ is defined as the y residuals from the first step $$u_2 = e_1$$

and X is replaced by the X residuals from the first step, $E_1$. The vectors $w_2$, $s_2$, and $l_2$ and the coefficient $b_2$ are calculated in the same manner. The $i^{th}$ step through the algorithm involves equating $u_i$ to the residual vector from the previous step, $e_{i-1}$, substituting the residual matrix $E_{i-1}$ for the X matrix, and calculating $w_i$, $s_i$, and $l_i$. The procedure continues until the y residuals are sufficiently small, i.e. until $e_1^t e_i$ reaches the desired level of error for the model. The matrices L and S are formed from the column vectors $l_i$ and $s_i$, and the coefficient vector b from the scalars $b_i$.

The residuals from the model are $$e = y - \hat{y} = y - Sb = y - SS^t y$$

The Standard Error of Estimate is $$SEE = \sqrt{e^t e/(n - k)}$$

For a new vector of independent variables $x_u$, the scalar estimate $y_u$ is obtained as $$x_u = Ls_u \rightarrow S_u = (L^t L)^{-1} L^t x_u = L^t x_u$$

$$y_u = s_u^t b = s_u^t (S^t S)^{-1} S^t y$$

Based on the model, the probability is a that the true value $y_u$ lies in range $$y_u - t \cdot SEE \cdot \sqrt{1 + d^2} \leq y_u \leq y_u + t \cdot SEE \cdot \sqrt{1 + d^2}$$

where t is the student's t distribution value for probability a and n−k degrees of freedom, and $d^2$ is given by $$d^2 = s_u^t (SS^t)^{-1} s_u$$

The PLS model can also be expressed in the form $$y = X^t p$$

where the regression vector p is $$p = Lb = L(S^t S)^{-1} S^t y = XS(S^t S)^{-2} S^t y$$

The regression vector is a linear combination of the columns of X.

1.4.3.3 Cross Validation:

The number of Principal Components or latent variables (i.e. the k dimension of the matrices U, Σ and V for PCR and of L and S for PLS) which are to be used in PCR or PLS models can be tested using a cross validation procedure. The X matrix is split into two matrices $X_1$ and $X_2$ which are of dimension f by n−j and f by j, respectively, where $1 \leq j \leq n/2$. y is similarly split into two corresponding vectors $y_1$ (dimension n−j) and $y_2$ (dimension j), e.g $$\text{if } X = \begin{pmatrix} x_{11} & x_{12} & x_{13} & x_{14} & x_{15} & x_{16} & x_{17} & x_{18} & x_{19} \\ x_{21} & x_{22} & x_{23} & x_{24} & x_{25} & x_{26} & x_{27} & x_{28} & x_{29} \\ x_{31} & x_{32} & x_{33} & x_{34} & x_{35} & x_{36} & x_{77} & x_{38} & x_{39} \\ x_{41} & x_{42} & x_{43} & x_{44} & x_{45} & x_{46} & x_{47} & x_{48} & x_{49} \end{pmatrix}$$

$$\text{and } y = \begin{pmatrix} y_1 \\ y_2 \\ y_3 \\ y_4 \\ y_5 \\ y_6 \\ y_7 \\ y_8 \\ y_9 \end{pmatrix}, \text{ then}$$

$$X_1 = \begin{pmatrix} x_{11} & x_{12} & x_{13} & x_{14} & x_{15} & x_{16} \\ x_{21} & x_{22} & x_{23} & x_{24} & x_{25} & x_{26} \\ x_{31} & x_{32} & x_{33} & x_{34} & x_{35} & x_{36} \\ x_{41} & x_{42} & x_{43} & x_{44} & x_{45} & x_{46} \end{pmatrix},$$

$$y_1 = \begin{pmatrix} y_1 \\ y_2 \\ y_3 \\ y_4 \\ y_5 \\ y_6 \end{pmatrix}, X_2 = \begin{pmatrix} x_{17} & x_{18} & x_{19} \\ x_{27} & x_{28} & x_{29} \\ x_{37} & x_{38} & x_{39} \\ x_{47} & x_{48} & x_{49} \end{pmatrix}, y = \begin{pmatrix} y_7 \\ y_8 \\ y_9 \end{pmatrix}$$

$$X_1 = \begin{pmatrix} x_{11} & x_{12} & x_{13} & x_{17} & x_{18} & x_{19} \\ x_{21} & x_{22} & x_{23} & x_{27} & x_{28} & x_{29} \\ x_{31} & x_{32} & x_{33} & x_{37} & x_{38} & x_{39} \\ x_{41} & x_{42} & x_{43} & x_{47} & x_{48} & x_{49} \end{pmatrix},$$

$$y = \begin{pmatrix} y_1 \\ y_2 \\ y_3 \\ y_7 \\ y_8 \\ y_9 \end{pmatrix}, X_2 = \begin{pmatrix} x_{14} & x_{15} & x_{16} \\ x_{24} & x_{25} & x_{26} \\ x_{34} & x_{35} & x_{36} \\ x_{44} & x_{45} & x_{46} \end{pmatrix}, y = \begin{pmatrix} y_4 \\ y_5 \\ y_6 \end{pmatrix}$$

$$X_1 = \begin{pmatrix} x_{14} & x_{15} & x_{16} & x_{17} & x_{18} & x_{19} \\ x_{24} & x_{25} & x_{26} & x_{27} & x_{28} & x_{29} \\ x_{34} & x_{35} & x_{36} & x_{37} & x_{38} & x_{39} \\ x_{44} & x_{45} & x_{46} & x_{47} & x_{48} & x_{49} \end{pmatrix},$$

$$y_1 = \begin{pmatrix} y_4 \\ y_5 \\ y_6 \\ y_7 \\ y_8 \\ y_9 \end{pmatrix}, X_2 = \begin{pmatrix} x_{11} & x_{12} & x_{13} \\ x_{21} & x_{22} & x_{23} \\ x_{31} & x_{32} & x_{33} \\ x_{41} & x_{42} & x_{43} \end{pmatrix}, y = \begin{pmatrix} y_1 \\ y_2 \\ y_3 \end{pmatrix}$$

would be three possible divisions of the matrices. Various models are built using $X_1$ and $y_1$, i.e. for PCR.

$$b = V_1^t y \text{ where } X_1 = U_1 \Sigma_1 V_1^t$$

and for PLS $$b = S_1^t y_1 \text{ where } X_1 = L_1 S_1^t$$

The number of columns retained in the $V_1$ and $S_1$ matrices in the models is varied over the range to be tested. The models are used to estimate the values for $y_2$. For PCR, a matrix $V_2$ is calculated from $$X_2 = U_1 \Sigma_1 V_2^t, \quad V_2 = X_2^t U_1 \Sigma_1$$

and the estimates are made as $$y_2 = V_2 b$$

For P1S, a matrix $S_2$ is calculated from $$X_2 = L_1 S_2^t, \quad S_2 = X_2^t L_1$$

and the estimates are made as $$y_2 = S_2 b$$

The prediction residuals are calculated as $$e_p = y_2 - y_2$$

The Predictive Residual Sum of Squares for this step is $$PRESS = e_p^t e_p$$

The procedure is repeated with different splits of X and y until each column of X and corresponding element in y have been in $X_2$ and $y_2$ once, e.g. using all three of the divisions of X and y show above. The total PRESS is the sum of the PRESS values calculated for each division. The optimum number of vectors to use in the model is that which minimizes the total PRESS.

1.4.3.4 Weighted Regression:

In applying linear least squares regression techniques to solve the regression equation $$y = X^t p + e$$

it is assumed that the elements of the residual vector are independent and normally distributed. In some applications, this assumption may not hold. For instance, if the elements $y_i$ of y are measured quantities, the error associated with the measurement of $y_i$ may depend on the magnitude of $y_i$. Alternatively, some of the individual $y_i$ values in y may represent the average of several measurements. In these cases, a weighted linear least square regression is used to develop the regression model.

If the quanity y is measured n times, then the average value $\bar{y}$ is $$\bar{y} = (y_1 + y_2 + \ldots y_n)/n$$

The quantity $s^2$, $$s^2 = [(y_1-\bar{y})^2 + (y_2-\bar{y})^2 + \ldots + (y_n-\bar{y})^2]/(n-1)$$

is an unbiased estimate of the variance in the measurement of y. s is the standard deviation in the measurement. As n approached $\infty$, $s^2$ approaches the true variance.

If each of the $y_i$ elements in vector y was measured once, and the measurement of $y_i$ is known to have variance $s_i^2$, then the regression equation relating y (dimension n) to V (dimension n by k) that provides for normally distributed residuals is given by $$Wy = WVb + e$$

where W is a n by n diagonal matrix whose elements are $$w_{ii} = 1/s_i$$

The coefficients are estimated as $$b = (V^t W^2 V)^{-1} V^t W^2 y$$

The estimate $\hat{y}$ is $$\hat{y} = Vb = V(V^t W^2 V)^{-1} V^t W^2 y$$

The residuals are $$e = y - \hat{y} = y - V(V^t W^2 V)^{-1} V^t W^2 y = (I - V(V^t W^2 V)^{-1} V^t W^2)y$$

If the variance in the measurement of all individual $y_i$ is the same, and $\bar{y}$ is a vector of dimension n whose individual elements $\bar{y}_i$ represent the average of $n_i$ measurements, then the weighting matrix for weighted least squares regression of $\bar{y}_i$ against V is given by $$w_{ii} = \sqrt{n_i}$$

individual measurement of element $y_i$ is $s_i^2$, then the weighting matrix for weighted least squares is defined by $$w_{ii} = \sqrt{n_i}/s_i$$

2.0 Definitions Relating to Quantitative Spectral Measurements:

If $i_o(f)$ is the intensity of electromagnetic radiation at frequency (wavelength) f which is incident on a sample, and i(f) is the intensity at the same frequency (wavelength) that is transmitted through the sample, then t(f), the transmission of the sample at frequency f is given by $$t(f) = i(f)/i_o(f)$$

The absorbance of the sample at frequency f is $$a(f) = -\log_{10}[t(f)]$$

The absorption spectrum of a sample will be repesented by a vector x of dimension f whose individual elements are the absorbance of the sample at each of f frequencies (wavelengths). For convenience, the elements in x are generally ordered in terms of increasing or decreasing frequency.

Quantitative spectral analysis is based on Beer's Law (4). For a mixture of chemical components, Beer's Law can be represented by the matrix equation $$x = Act \text{ or } x/t = Ac$$

where A is an f by c matrix whose columns are the absorption spectra $a_i$ of the c individual pure components (measured at unit pathlength), where c is a vector whose elements are the concentrations of the components in the mixture, and where t is a scalar representing the pathlength (thickness) of the sample.

Beer's Law implies a linear relationship between the measured absorption spectrum, and the concentrations of mixture components. If the spectra of the components is known, the equation for Beer's Law can be solved for the component concentrations, i.e.

$$(A^t A)^{-1} A^t x/t = c$$

If y is a property of the sample that depends linearly on the concentrations of the sample components, then $$y = r^t c = r^t (A^t A)^{-1} A^t x/t$$

where r is the vector of coefficients that define the linear dependence. This expression indicates that there is a linear relationship between the property and the absorption spectrum of the sample.

In general, the vectors in the matrix A are not known, and the relationship between component concentrations and/or properties and the sample spectrum is represented by $$y = p^t x = x^t p$$

where p is vector of dimension f that relates the spectrum to the desired concentration or property. The objective of quantitative spectral analysis is to define the vector p.

2.1 Calibration:

Calibration is the process of creating a regression model to relate the component concentration and/or property data to the absorption spectra. The calibration of a spectral model will generally consist of the following steps:

[1] n representative samples of the materials for which the model is to be developed will be collected, their absorption spectra ($x_i$, i=1,n) will be obtained, and the component concentrations and/or property data ($y_i$, i=1,n) will be measured. The samples that are used in the calibration are referred to as references, and the spectra of these samples are referred to as reference spectra.

2] A regression model of the form $$y = X^t p + e$$

will be constructed for each component and/or property which is to be modeled, where y is the vector of dimension n containing the individual concentration or property values for the n reference samples, and X if a f by n matrix whose columns are the spectra of the n reference samples measured at f frequencies (wavelengths). The mathematical method that is used in calculating the regression model will depend on the number of reference samples relative to the number of frequencies (wavelengths).

2.1.1 Calibration Models for $f \leq n$:

If the number of reference samples, n, used in the calibration exceeds the number of frequencies per spectrum, f, then the calibration model can be obtained via linear least square regression (section 1.4.2).

$$y = X^t p + e \rightarrow (XX^t)^{-1} Xy = (XX^t)^{-1} XX^t p + (XX^t)^{-1} Xe = p + (XX^t)^{-1} Xe$$

The regression model could also be obtained using PCR or PLS, but in this case, these methods aren't required since the $(XX^t)$ matrix can be inverted.

If the number of frequencies (wavelengths) per spectrum, f, exceeds the number of reference samples, n, then a subset of f' frequencies can be chosen such that $f' \leq n$, and linear least square regression can be used to develop the calibration model $$y = X'^t p + e \rightarrow (X'X'^t)^{-1} X'y = p + (X'X'^t)^{-1} X'e$$

where X' is the f' by n matrix obtained from X by deleting the f-f' rows. The choice of the frequencies (wavelengths) that are to be used in developing the regression model can be based on a prior knowledge of the component absorptions present in the spectra (i.e. spectroscopy expertise), or they can be chosen using a statistical wavelength (frequency) selection algortihm (5).

If the concentration and/or property data in y does not have uniform measurement variance, and/or represents the average of differing numbers of experimental measurements, then the calibration model can be developed using a weighted linear least squares regression (section 1.4.3.4).

2.1.2 Calibration Models for $f \geq n$:

If the number of frequencies per spectrum, f, exceeds the number of reference spectra used in the calibration, n, then the calibration model can be built using either Principal Components Regression (section 1.4.3.1)

$$y = X^t p + e \rightarrow U\Sigma^{-1}V^t y = U\Sigma^{-1}V^t X^t p + U\Sigma^{-1}V^t e = p + U\Sigma^{-1}V^t e$$

or via Partial Least Square Regression (section 1.4.3.2)

$$y = X^t p + e \rightarrow X = LS^t, \; b = (S^t S)^{-1} S^t y \rightarrow p = Lb$$

For Principal Components Regression, the model may be developed using a two step calculation $$X = U\Sigma V^t,$$
$$y = Vb \rightarrow p = U\Sigma^{-1}V^t y = XV\Sigma^{-2}V^t y = XV\Sigma^{-2}b$$

where the nonzero coefficients, $b_i$, which are used in the model may be determined using step-wise or PRESS based regressions (section 1.4.3.2). If the individual component concentrations and/or properties in y are of unequal measurement variance, or represent the average of unequal numbers of experimental determinations, then the step-wise or PRESS based regression may be conducted using the matrices from the weighted least squares regression (section 1.4.3.4).

2.2 Analysis of Unknowns:

All of the above mentioned calibration models can be expressed in the form $$y = X^t p$$

The models differ in the means used to estimate the regression vector p. If $x_u$ represents the spectrum of a new, unknown material, then the component concentrations and/or properties estimated using the model are $$y_u = x_u^t p$$

The use of the calibration model to estimate component concentrations and/or properties is referred to as analysis.

3.0 Constrained Spectral Analysis:

The spectrum measured for a sample, x, generally represents the superposition of the absorptions due to the sample components, $x_c$, and signals arising from the process involved in making the spectral measurement, m.

$$x = x_c + m$$

The signal arising from the measurement process may be the sum of various individual signals, $m_i$ $$x = x_c + m_1 + m_2 + \ldots + m_s$$

Examples of these measurement process signals would include, but not be limited to,

[1] reflection and/or scattering loses from the windows of the cell used to contain the sample, or in the case of free-standing samples, from the front surface of the sample;

[2] variations in the spectral baseline arising from variations in the intensity (temperature) of the spectrometer sourse and/or the responsivity of the spectrometer detector;

[3] absorption signals arising from gas phase components (e.g. water vapor and carbon dioxide) that are present in the light path through the spectrometer, but are not sample components. Since the regression vectors calculated from the calibration are in all cases linear combinations of the original spectra, i.e.

for linear least squares, $p = X^t (XX^t)^{-1} Xy$ for PCR, $p = U\Sigma^{-1}V^t y = XV\Sigma^{-2}V^t y$ and for PLS, $p = Lb = XS(S^t S)^{-1} b$ they will include contribution from the measurement process signals, m. As such, the estimation of component concentrations and/or property values based on $$y_u = x_u^t p$$

will vary not only with changes in the absorptions due to real sample components, but also with variations in the signals arising from the measurement process. The calibration models are thus not robust relative to variations in the signals arising from the measurement process.

The estimation of component concentrations and/or properties can be expressed as $$y_u = x_u^t p = x_c^t p + m^t p$$

The estimation will be insensitive to variations in the signals arising from the measurement process if, and only if, the second term, $m^t p$, is equal to zero, i.e. if the regression vector is orthogonal to the signals arising from the measurement process.

2.1 Constrained Linear Least Squares:

If X is an f by n matrix containing the spectra of the reference samples, X can be represented as the sum $$X = X_c + MN^t$$

where M is a f by s matrix containing the individual signals arising from the measurement process as columns, and N is a n by s matrix containing the scalar elements $n_{ij}$ which correspond to the level of the $j^{th}$ measurement process signal for the $i^{th}$ reference sample. If $f < n$ (or if $f' < n$ frequencies are chosen), then the solution to the calibration model $$y = X^t p + e$$

which yields a regression vector p which is orthogonal to the measurement process signals M is derived via a constrained least squares regression, where the constrain equation is $$M^t p = 0$$

where 0 is a zero vector. X' is defined as the f by n+s matrix obtained by adding the s columns of M to X, and y' is the vector of dimension n+s obtained by adding a corresponding s zero elements to y. The constrained least square solution is then $$p = (X'X'^t)^{-1} X'y' - (X'X'^t)^{-1} M(M^t M)^{-1} M^t X'y'$$

$$p = (X'X'^t)^{-1} [I - M(M^t M)^{-1} M^t] X'y'$$

$$p = [I - M(M^t M)^{-1} M^t](X'X'^t)^{-1} X'y'$$

The estimate y is then $$y = X^t p = X_c^t p + N M^t p$$

$$y = X_c^t [I - M(M^t M)^{-1} M^t](X'X'^t)^{-1} X'y' + NM^t [I - M(M^t M)^{-1} M^t](X'X'^t)^{-1} X'y'$$

$$y = X_c^t [I - M(M^t M)^{-1} M^t](X'X'^t)^{-1} X'y' + NM^t (X'X'^t)^{-1} X'y' - NM^t M(M^t M)^{-1} M^t (X'X'^t)^{-1} X'y'$$

$$y = X_c^t [I - M(M^t M)^{-1} M^t](X'X'^t)^{-1} X'y' + NM^t (X'X'^t)^{-1} X'y' - NM^t (X'X'^t)^{-1} X'y'$$

$$y = X_c^t [I - M(M^t M)^{-1} M^t](X'X'^t)^{-1} X'y'$$

The estimate y is constrained to be independent of the presence of the measurement process signals. Similarly, it $x_u$ is a spectrum of a new unknown sample, such that $$x_u = x_c + Mn$$

then the estimation of $y_u$ is $$y_u = x_u^t p = (x_c + Mn)^t p$$

$$y_u = x_c^t [I - M(M^t M)^{-1} M^t](X'X'^t)^{-1} X'y' + nM^t [I - M(M^t M)^{-1} M^t](X'X'^t)^{-1} X'y'$$

$$y_u = x_c^t [I - M(M^t M)^{-1} M^t](X'X'^t)^{-1} X'y'$$

i.e. the estimate is independent of the presence of the measurement process signals in the spectrum $x_u$. The residuals from the model are $$e = y - y = y - X^t [I - M(M^t M)^{-1} M^t](X'X'^t)^{-1} X'y'$$

The Standard Error of Estimate is $$SEE = \sqrt{e^t e/(n - f)}$$

Based on the model, the probability is a that the true value $y_u$ lies in range $$y_u - t \cdot SEE \cdot \sqrt{1 + d^2} \leq y_u \leq y_u + t \cdot SEE \cdot \sqrt{1 + d^2}$$

where t is the student's t distribution value for probability and n−f degrees of freedom, and $d^2$ is given by $$d^2 = x_u^t (X'X'^t)^{-1} M[M^t (M^t M)^{-1} M]^{-1} M^t x_u$$

2.2 Constrained Principal Components Regression:

If $f > n$, then the constrained linear least squares solution in section 2.1 cannot be used since the matrix $XX^t$ is at most of rank n, is singular, and cannot be directly inverted. It is possible to develop a constrained principal components model by following a similar methodology. If X' again represents the f by n+s matrix whose first s columns are measurement process signals, M, and whose last n columns are the reference spectra, then the singular value decomposition of X' is $$X' = U'\Sigma' V'^t$$

where U' is an f by k matrix, $\Sigma'$ is the k by k matrix of singular values and V' is an n+s by k matrix. The s by k matrix $V_m$ corresponds to the first s rows of V', i.e. to the right eigenvectors associated with the signals due to the measurement process. The measurement process signals can be expressed as $$M = U'\Sigma' V_m^t$$

If y' is the vector containing the s zeros and the n concentration or property values, then the regression $$y' = V b + e$$

subject to the constraint $$V_m b = 0$$

yields estimated coefficients of the form $$b = [I - V_m^t (V_m V_m^t)^{-1} V_m](V'^t V')^{-1} V'^t y' = [I - V_m^t (V_m V_m^t)^{-1} V_m] V'^t y'$$

The regression vector is then $$p = U'\Sigma'^{-1} [I - V_m^t (V_m V_m^t)^{-1} V_m] V'^t y'$$

$$p = U'\Sigma'^{-1} V'^t y' - U'\Sigma'^{-1} V_m^t (V_m V_m^t)^{-1} V_m V'^t y'$$

The estimate y for the model is $$y = X^t p = X_c^t p + NM^t p$$

$$y = X_c^t [U'\Sigma'^{-1} V'^t y' - U'\Sigma'^{-1} V_m^t (V_m V_m^t)^{-1} V_m V'^t y'] + NM^t [U'\Sigma'^{-1} V'^t y' - U'\Sigma'^{-1} V_m^t (V_m V_m^t)^{-1} V_m V'^t y']$$

$$y = X_c{}^t[U'\Sigma'^{-1}V^t y' - U'\Sigma'^{-1}V_m{}^t(V_m V_m{}^t)^{-1}V_m V^t y'] + NV_m\Sigma' U'^t[U'\Sigma'^{-1}V^t y' - U'\Sigma'^{-1}V_m{}^t)V_m V_m{}^t)^{-1}V_m V^t y']$$

$$y = X_c{}^t[U'\Sigma'^{-1}V^t y' - U'\Sigma'^{-1}V_m{}^t(V_m V_m{}^t)^{-1}V_m V^t y'] = NV_m\Sigma' U'^t U'\Sigma'^{-1}V^t y' - NV_m\Sigma' U'^t U'\Sigma'^{-1}V_m{}^t(V_m V_m{}^t)^{-1}V_m V^t y'$$

$$y = X_c{}^t[U'\Sigma'^{-1}V^t y' - U'\Sigma'^{-1}V_m{}^t(V_m V_m{}^t)^{-1}V_m V^t y'] + NV_m V^t y' - NV_m V_m{}^t(V_m V_m{}^t)^{-1}V_m V^t y'$$

$$y = X_c{}^t[U'\Sigma'^{-1}V^t y' - U'\Sigma'^{-1}V_m{}^t(V_m V_m{}^t)^{-1}V_m V^t y']$$

The estimated concentration and property values are constrained to be independent of the signals that are due to the measurement process.

For an unknown material with spectrum $x_u$, $$x_u + x_c + Mn = x_c + U'\Sigma' V_m{}^t n \rightarrow y_u = x_u{}^t p = (x_c + Mn)^t p$$

$$y_u = x_c{}^t[U'\Sigma'^{-1}V^t y' - U'\Sigma'^{-1}V_m{}^t(V_m V_m{}^t)^{-1}V_m V^t y'] + nM^t[U'\Sigma'^{-1}V^t y' - U'\Sigma'^{-1}V_m{}^t(V_m V_m{}^t)^{-1}V_m V^t y']$$

$$y_u = x_c{}^t[U'\Sigma'^{-1}V^t y' - U'\Sigma'^{-1}V_m{}^t(V_m V_m{}^t)^{-1}V_m V^t y'] = nV_m\Sigma' U'^t U'\Sigma'^{-1}V^t y' - nV_m\Sigma' U'^t U'\Sigma'^{-1}V_m{}^t(V_m V_m{}^t)^{-1}V_m V^t y'$$

$$y_u = x_c{}^t[U'\Sigma'^{-1}V^t y' - U'\Sigma'^{-1}V_m{}^t)(V_m V_m{}^t)^{-1}V_m V^t y']$$

The estimated concentrations and properties are independent of the measurement process signal. The residuals from the model are $$e = y - \hat{y} = y - X^t p = y - X^t U'\Sigma'^{-1}[I - V_m{}^t(V_m V_m{}^t)^{-1}V_m]V^t y'$$

The Standard Error of Estimate is $$SEE = \sqrt{e^t e/(n-k)}$$

Based on the model, the probability is a that the true value $y_u$ lies in range $$\hat{y}_u - t \cdot SEE \cdot \sqrt{1+d^2} \leq y_u \leq \hat{y}_u + t \cdot SEE \cdot \sqrt{1+d^2}$$

where t is the student's t distribution value for probability a and n−f degrees of freedom, and $d^2$ is given by $$d^2 = v_u[I - V_m{}^t(V_m V_m{}^t)^{-1}V_m]v_u{}^t$$

The Constrained Principal Components Regression described above will yield a stable calibration model that is robust to variations in the intensity of signals arising from the measurement process provided that the scaling of the measurement process signals in M is sufficiently large that principal components corresponding to these measurement process signals are retained in the first k principal components that are used in the model. If the scaling of the signals in M is too small, then the matrix $V_m V_m{}^t$ will be singular and cannot be inverted.

An alternative, equivalent, and preferred method for developing a Constrained Principal Components model involves orthogonalizing the spectra in X to the measurement process signals in M prior to the development of the model. X is a f by n matrix containing the spectra of the n reference samples at f frequencies. M is a f by s matrix containing the spectra of the s measurement process signals at the f frequencies. The first step in the process is to derive a set of orthogonal vectors, the columns of the matrix $U_m$, that represent the original measurement process signals in M. This can be accomplished by either using a Gram-Schmidt orthogonalization procedure, a singular value decomposition of M, or some combination of the two. For example, the singular value decomposition of M would yield $$M = U \ \Sigma \ V_m{}^t$$

where U is f by s, $\Sigma$ is s by s, and V is s by s. Each spectrum in X is then orthogonalized to the columns of U to obtain the corrected spectra, $X_c$. If $x_1$ is the first spectrum in X, and $u_1, u_2, \ldots u_s$ are the orthogonalized measurement process signals, then the first corrected spectrum, $c_1$, is given by $$c_1 = x_1 - u_1(u_1{}^t x_1) + u_2(u_2{}^t x_1) + \ldots + u_s(u_s{}^t x_1)$$

The matrix form of this orthogonalization is $$X_c = X - U \ U_m{}^t X$$

where the individual corrected spectra, $c_i$, are the columns of the $X_c$ matrix. The original spectral matrix is given by $$X = X_c + U \ U_m{}^t X$$

In the next step, the singular value decomposition of $X_c$ is then obtained as $$X_c = U_c \Sigma_c V_c{}^t$$

The regression model can then be obtained directly as $$y = X_c{}^t p + e \rightarrow p = U_c \Sigma_c{}^{-1} V_c{}^t y$$

or indirectly by using the relationship $$y = V_c b + e \rightarrow b = V_c{}^t y$$

The estimate y from the model is $$\hat{y} = X^t p = X^t U_c \Sigma_c{}^{-1} V_c{}^t y = (X_c + U \ U_m{}^t X)^t U_c \Sigma_c{}^{-1} V_c{}^t y$$

$$\hat{y} = X_c{}^t U_c \Sigma_c{}^{-1} V_c{}^t y + X^t U \ U_m{}^t U_c \Sigma_c{}^{-1} V_c{}^t y = X_c{}^t U_c \Sigma_c{}^{-1} V_c{}^t y$$

The term containing the product $U_m{}^t U_c$ is zero since the columns of $U_c$ are linear combinations of the columns of $X_c$ which where generated to be orthogonal to the columns of U. The estimate is constrained to be insensitive to the intensity of the measurement process signals in X. The residuals for the model are $$e = y - \hat{y} = y - X_c{}^t U_c \Sigma_c{}^{-1} V_c{}^t y$$

The Standard Error of Estimate for the model is $$SEE = \sqrt{e^t e/(n-k)}$$

For a new unknown sample with spectrum $x_u$ which unknown measurement process signals nM, the estimate of $y_u$ is $$y_u = x_u^t p = (x_c^t + Mn)^t U_c \Sigma_c^{-1} V_c^t y =$$
$$(x_c^t + U \ \Sigma \ V_m^t n)^t U_c \Sigma_c^{-1} V_c^t y$$

$$y_u = x_c^t U_c \Sigma_c^{-1} V_c^t y + n^t V \ \Sigma \ U_m^t U_c \Sigma_c^{-1} V_c^t y =$$
$$x_c^t U_c \Sigma_c^{-1} V_c^t y = v_c^t V_c^t y$$

where $$v_c^t = x_c^t U_c \Sigma_c^{-1}$$

The estimate depends only on the portions of the spectra arising from the component absorptions, $x_c$, and is independent of the measurement process signals. Based on the model, the probability is a that the true value $y_u$ lies in range $$y_u - t \cdot SEE \cdot \sqrt{1 + d^2} \leq y_u \leq y_u + t \cdot SEE \cdot \sqrt{1 + d^2}$$

where t is the student's t distribution value for probability c, and $n-f$ degrees of freedom, and $d^2$ is given by $$d^2 = v_c^t v_c$$

Individual $b_i$ used in the regression of y versus $V_c$ can be set to zero based on the results of a step-wise or PRESS based regression if doing so does not result in a statistically significant increase in the residual sum of squares. If the individual elements of y represent measurements having differing measurement variance, or are the averages of differing numbers of measurments, the regression of y versus $V_c$ can be accomplished using a weighted regression. In the weighted regression, a step-wise or PRESS based algorithm can again be employed to test whether individual coefficients can be set to zero.

The equivalence of the two methods of calculating a Constrained Principal Components Regression model can be demonstrated as follows: If the first s columns of X' that correspond to the measurement process signals M are scaled by a sufficiently large value such that the variance due to M (the sum of the diagonal elements of $M^t M$) is much larger than the variance due to the reference spectra (the sum of the diagonal elements of $X^t X$) then the first s Principal Components of X' will be U, and the remaining k Principal Components will be $U_c$, i.e.

$$X' = U'\Sigma' V'^t = (U_m, U_c)(\Sigma_m, \Sigma_c)(V_m, V_c)^t$$

where (U ,$U_c$) is an f by s+k matrix whose first s columns are U and whose last k columns are $U_c$, ($\Sigma$ ,$\Sigma_c$) is an s+k by s+k matrix whose first s diagonal elements are from $\Sigma_m$ and whose last k diagonal elements are from $\Sigma_c$, and (V ,$V_c$) is an s+k by s+n matrix whose first s columns are V and whose last n columns are $V_c$. The regression vector is then $$p = U'\Sigma'^{-1} V^t y' - U'\Sigma'^{-1} V_m^t (V_m V_m^t)^{-1} V_m V^t y'$$

$$p = (U, U_c)(\Sigma, \Sigma_c)^{-1}(V, V_c)^t y' - (U, U_c)$$
$$(\Sigma, \Sigma_c)^{-1} V_m^t (V_m V_m^t)^{-1} V_m (V, V_c)^t y'$$

$$p = U \ \Sigma^{-1} V^t y + U_c \Sigma_c^{-1} V_c^t y - U \ \Sigma^{-1}$$
$$V_m^t (V_m V_m^t)^{-1} V_m^t y_m - U_c \Sigma_c^{-1} V_m^t (V_m V_m^t)^{-1} V_m V_c^t y'$$

$$p = U \ \Sigma^{-1} V^t y + U_c \Sigma_c^{-1} V_c^t y -$$
$$U \ \Sigma^{-1} V_m^t y = U_c \Sigma_c^{-1} V_c^t y$$

where the term $U_c \Sigma_c^{-1} V_m^t (V_m V_m^t)^{-1} V_m V_c^t y'$ is zero since the columns of $V_m$ and $V_c$ are orthogonal. The Constrained Principal Components model obtained using the constrained regression method is equivalent to that obtained using the preorthogonaliztion method providing the scaling of the measurement process signals is large enough to ensure that they are included in Principal Components that are retained from the singular value decomposition of X'. The preorthogonalization method is preferred since it avoids the necessity of determining an appropriate scaling for the measurement process signals, and it avoids potential computer round off errors which can result if the scaling of the measurement process signals is too large relative to the scaling of the spectra.

Constrained Principal Components Regression can be employed in the case where $f \leq n$, but it is not required since the matrices required for solving the constrained linear least squares model can be inverted.

2.2 Constrained Partial Least Squares Regression:

If $f > n$, then the constrained linear least squares solution in section 2.1 cannot be used since the matrix $XX^t$ is at most of rank n, is singular, and cannot be directly inverted. It is possible to develop a constrained partial least squares model by following a similar methodology. X is a f by n matrix containing the spectra of the n reference samples at f frequencies. M is a f by s matrix containing the spectra of the s measurement process signals at the f frequencies. The first step in the development of the constrained partial least square model is to derive a set of orthogonal vectors, the columns of the matrix U , that represent the original measurement process signals in M. This can be accomplished by either using a Gram-Schmidt orthogonalization procedure, a singular value decomposition of M, or some combination of the two. For example, the singular value decomposition of M would yield $$M = U \ \Sigma \ V_m^t$$

where U is f by s, $\Sigma$ is s by s, and V is s by s. Each spectrum in X is then orthogonalized to the columns of U to obtain the corrected spectra, $X_c$. If $x_1$ is the first spectrum in X, and $u_1, u_2, \ldots u_s$ are the orthogonalized measurement process signals, then the first corrected spectrum, $c_1$, is given by $$c_1 = x_1 - u_1(u_1^t x_1) + u_2(u_2^t x_1) + \ldots + u_s(u_s^t x_1)$$

The matrix form of this orthogonalization is $$X_c = X - U \ U_m^t X$$

where the individual corrected spectra, $c_i$, are the columns of the $X_c$ matrix. The original spectral matrix is given by $$X = X_c + U \ U_m^t X$$

A partial least squares model is then developed to relate $X_c$ and y $$X_c = L_c S_c^t \rightarrow y = S_c b + e$$

where S is a n by k matrix, L is a f by k matrix. The model is developed using the methodology described in section 1.4.3.2. The regression vector obtained is $$p = L_c b = X_c S_c (S_c^t S_c)^{-1} S_c^t y$$

The estimate y based on the model is $$y = X^t p = (X_c + MN)^t p = (X_c + U \Sigma V_m^t N)^t p = X_c^t p + (U \Sigma V_m^t N)^t p$$

$$y = X_c^t X_c S_c (S_c^t S_c)^{-1} b + N^t V \Sigma U_m^t X_c S_c (S_c^t S_c)^{-1} b = X_c^t X_c S_c (S_c^t S_c)^{-1} b$$

where the term $N^t V \Sigma U_m^t X_c S_c (S_c^t S_c)^{-1} b$ is zero since the columns of U are orthogonal to the columns of $X_c$. The estimate y is constrained to be independent of the measurment process signals. The residuals from the model are $$e = y - \hat{y} = y - X_c^t X_c S_c (S_c^t S_c)^{-1} b$$

The Standard Error of Estimate for the model is $$SEE = \sqrt{e^t e/(n - k)}$$

For a new spectrum, $x_u$, which contains component absorptions $x_c$ and measurment process signals Mn, the scalar estimate $y_u$ is obtained as $$s_u = (L_c^t L_c)^{-1} L_c^t x_u = (L_c^t L_c)^{-1} L_c^t (x_c + Mn) = (L_c^t L_c)^{-1} L_c^t (x_c + U \Sigma V_m^t n)$$

$$s_u = (L_c^t L_c)^{-1} L_c^t x_c = L_c^t x_c$$

$$y_u = s_u^t b = x_c^t L_c (S_c^t S_c)^{-1} S_c^t y$$

The estimate of $y_u$ is constrained so as to be independent of an measurment process signals in $x_u$. Based on the model, the probability is a that the true value $y_u$ lies in range $$\hat{y}_u - t \cdot SEE \cdot \sqrt{1 + d^2} \leq y_u \leq \hat{y}_u + t \cdot SEE \cdot \sqrt{1 + d^2}$$

where t is the student's t distribution value for probability a and n−k degrees of freedom, and $d^2$ is given by $$d^2 = s_u^t (S_c^t S_c)^{-1} s_u$$

3.0 Pathlength and Scaling Constraints:

The matrix form of Boer's Law can be represented by the equation $$X = ACT \text{ or } XT^{-1} = AC \text{ or } (A^t A)^{-1} A^t X T^{-1} = C \rightarrow C^t = T^{-1} X^t A (A^t A)^{-1}$$

where X is the f by n matrix containing the reference spectra used in the development of spectral calibrations, A is an f by c matrix hose columns are the absorption spectra $a_i$ of the c individual components (measured at or normalized to unit pathlength), where C is a c by n matrix whose general element $c_{ij}$ the concentration of the $i^{th}$ component in the $j^{th}$ reference sample, and where T is a diagonal n by n matrix containing the pathlengths for the n samples.

If y is a component concentration or a property that depends linearly on the concentrations of all the sample components, then $$y = C^t r$$

where r is a vector of dimension c which the coefficients relating y to the concentrations of the individual components. If y is the concentration of a single component, the only the one corresponding element of r will be nonzero. If y is the concentration of a "lumped" component (e.g. the total aromatics content of a hydrocarbon which equals the sum of the concentrations of the individual aromatic components), then the elements of r which correspond to the components that were "lumped" will be one, and the remaining elements of r will be zero. If y is a physical property (i.e. a property that depends on the physical state of the samples, e.g. the sample density measured at a specified temperature) or a performance property (i.e. a property that is defined by the use of the sample in an application, e.g. the research octane number of a gasoline as defined by ASTM 2699-84 (6), or the reactivity of the sample under a defined set of conditions), then r contains the coefficients that relate the property to all of the individual components. The regression models that are developed above have the form $$y = C^t r + e = T^{-1} X^t A (A^t A)^{-1} r = T^{-1} X^t p + e \rightarrow A(A^t A)^{-1} r = p$$

If all the reference spectra are collected at the same pathlength, then T and $T^{-1}$ are the products of scalars times the unit matrix I, and the regression equation becomes $$y = T^{-1} X^t A (A^t A)^{-1} r + e = I X^t A (A^t A)^{-1} rt = X^t p + e \rightarrow A(A^t A)^{-1} rt = p$$

where t is the pathlength used in all the measurements. In this case, the scalar t is lumped into the overall regression vector that is determined in the calibration. During the analysis, the unknown spectrum must be collected at the same pathlength, or if it is collected at a different pathlength t', either the spectrum $x_u$ or the estimated value $y_u$ must be scaled by the ratio t/t'.

If all the reference spectra are not collected at the same pathlength, then the spectra can be normalized prior to the calibration, $$X_n = X T^{-1}$$

and the regression model can built relating the normalized data $X_n$ to y. In this case, during the analysis, either the unknown spectrum $x_u$ or the intial estimate of $y_u$, must be scaled by 1/t' (the pathlength used in the collection of $x_u$) to obtain the final estimate.

The sum of all the individual components in the sample must equal unity, i.e. they must account for the total sample. If r is a vector containing all ones, then y is also $$y = C^t r = C^t 1 = 1$$

where 1 indicates a vector containing all ones. In this case, a regression of the form $$y = 1 = T^{-1} X^t p_t \rightarrow 1T = X^t p_t \rightarrow t = X^t p_t$$

where t is a vector containing the pathlengths used in the measurement of the n reference samples. $p_t$ is a regression vector that can be used to estimate the pathlength used in the measurement of the spectrum of an unknown, i.e.

$$t = x_u^t p_t$$

The use of a regression model to estimate the pathlength at which a spectrum was collected assumes that all the components in the sample contribute a measurable absorption to the spectrum. If a component possesses no absorptions in the spectral range used in the calibration, then an increase or decrease in the concentration of the component produces at most a change in the scaling of the spectrum (via changing the concentrations of the other components where the sum of the component concentrations sums to unity, i.e. dilution effects), and cannot be distinguished from a scaling change associated with varying the pathlength. The assumption required for use of a pathlength regression is valid for mid- and near-infrared spectroscopies where all typical sample components are expected to give rise to some vibrational absorption, but it would not hold for ultraviolet-visible spectroscopy where some components might possess no measurable absorption. If reference and unknown samples are diluted in solvent for the collection of the IR spectra, the pathlength regression can still be applies since the solvent can be considered as an additional sample component.

The results of a pathlength regression model can be incorporated into the calibration models built for the estimation of component concentrations and/or properties. If X is the matrix containing reference spectra collected at pathlengths t, then a regression model can be constructed to estimate t $$t = X^t p_t + e \rightarrow t = X^t p_t$$

where $p_t$ can be estimated using Linear Least Square Regression, Principal Components Regression, Partial Least Squares Regression, or more preferably Constrained Linear Least Squares Regression, Comstrained Principal Components Regression or Contrained Partial Least Squares Regression. The matrix T is defined as a diagonal matrix whose element $t_{ii}$ is the estimate $t_i$ from t, i.e. the $t_{ii}$ is the estimated pathlength for the $i^{th}$ sample. Regression models for component concentrations and/or properties can be developed using the equation $$y = T^{-1} X^t p + e = X_t^t p + e$$

where $X_t$ is the reference spectral data scaled by the estimated pathlengths.

For Linear Least Squares Regression, or Constrained Linear Least Squares Regression, the incorporation of the pathlength regression into the calibration is relatively straight forward. A model is built based on the raw reference spectra, X, and the pathlengths, t. The model is applied to the reference spectra to estimate the pathlengths, t. The estimated pathlengths are used to calculate T and to rescale the data to obtain $X_t$. Models are then built for all the components and/or properties y based on the rescaled spectral data, $X_t$. During the analysis, the pathlength used in the collection of the spectrum of the unknown, $t_u$, is estimated, and either the spectrum of the unknown, or the initial estimates of the component concentrations and/or properties are scaled by $1/t_u$.

In Partial Least Squares Regression and Constrained Partial Least Squares regression, the pathlength, component concentration, or property values are used in the calculation of the decomposition of X. The matrices L and S which are calculated are different for each component, property and for pathlength. Separate models must thus be constructed for pathlength and for components and properties. A general calibration procedure would involve, developing a model for the pathlengths t based on the raw reference spectra X. Using the estimates t to construct the T matrix and scaling X to obtain $X_t$. Building regression models for each component and/or property y based on $X_t$. In the analysis of a spectrum $x_u$ of an unknown, the pathlength $t_u$ would first be estimated, and then either the spectrum or the initial estimates of the components and/or properties would be scaled by $1/t_u$.

For Principal Components Regression and Constrained Principal Components regression, a more computationally efficient procedure is preferred. The matrix X (or $X_c$ for Constrained PCR) is decomposed as $$X = U \Sigma V^t$$

The pathlengths are then regressed as $$t = V b_t + e \rightarrow b_t = V^t t \rightarrow t = V b_t$$

The matrix T is formed by placing the elements of t on the diagonal, and the component concentrations and/or properties are regressed as $$y = T^{-1} V b + e \rightarrow b = (V^t T^{-2} V)^{-1} V^t T^{-1} y$$

For an unknown material with spectrum $x_u$, the pathlength used in collection the spectrum is estimated as $$x_u = U \Sigma v_c \rightarrow t_u = v_c^t b_t$$

The component concnetrations and/or properties are then estimated as $$y_u = v_c^t b / t_u$$

The alternative to the above method would involve calculating the singular value decomposition of $X_t$ (the spectra scaled to the estimated pathlengths) to build regression models for y. Since the matrices produced by the singular value decomposition of X (or $X_c$) are required for the pathlength estimation, the singular value decomposition of $X_t$ would produce a second set of matrices which would have to be stored and recalled for the estimation of components and/or properties. By conducting only one singular value decomposition, the above method reduces the computer memory, disk storage, input/output requirements and computation time for conducting the calibrations and analyses.

The regression for the pathlength can be conducted using a step-wise or PRESS based method to detect coefficients that are statistically equivalent to zero. A weighted regression may be employed in the development of the regression models for the component concentrations and/or properties in the case where the individual elements if y are of unequal measurement variance, and/or represent the average of differing numbers of individual experimental determinations. A step-wise or PRESS based method can also be employed to conduct these regressions.

4.0 Preferred Method for Calculating the Measurement Process Singnal Matrix:

The matrix U used in calculation of the Constrained Principal Components Regression and the Constrained Partial Least Square Regression is derived from a matrix M which contains examples of the signals arising from the measurement process. The columns of M will generally consist of two types, calculated spectra which are used to simulate certain types of measurement process signals, and experimental spectra collected so as to provide an example of one or more measurement process signals. The calculated spectra could include, but not be limited to, frequency (or wavelength) dependent polynomials which are used to approximate variations in the baseline of the absorption spectra. Such baseline variations can result from variations in the reflection and/or scattering from the front face of the sample or cell, from variations in the responce of the spectrometer detector, or from variations in the intensity of the spectrometer source. An example of the experimental spectra which can be used would include, but not be limited to, the spectra of atmospheric water vapor, and/or carbon dioxide. These type of experimental spectra are referred to as correction spectra.

The following is an example of one computational method for arriving at the U matrix. If the reference spectra X are collected over a frequency (wavelength) range from $\nu_1$ to $\nu_2$ at interval $\Delta \nu$, then a set of orthogonal polynomials over the spectral range can be constructed using Legendre polynomials $$P_k(\xi) = \frac{1}{2^k k!} \frac{d^k}{d\xi^k} (\xi^2 - 1)^k$$

where $\xi$ is defined as $$\xi = (\nu - \nu_2)/(\nu_1 - \nu_2)$$

The elements $u_{ij}$ of the $U_p$ polynomial vectors are calculated as $$u_{ij} = P_k(\xi)/\sqrt{f} = \frac{1}{2^k k! \sqrt{f}} \frac{d^k}{d\xi^k} (\xi^2 - 1)^k$$

where $\xi = (\nu_1 + (i - 1) \cdot \Delta \nu - \nu_2)/(\nu_1 - \nu_2)$ where j is equal to k+1 and the $\sqrt{f}$ is required so that the columns of $U_p$ are normalized. The elements of the first column of $U_p$ correspond to $P_0(\xi)$, and are constants of the value of $1/\sqrt{f}$. The second column of $U_p$ depends linearly on frequency, the third has a quadratic dependency of frequency, etc.. The column vectors of $U_p$ form an orthonormal set, i.e.

$$U_p^t U_p = I$$

The matrix $U_p$ is of dimension f by p, where p is the number of polynomial terms being used to model background variations, and p−1 is the highest degree of the polynomial.

Z is an f by z matrix containing z experimental spectra representing measurment process signals for which constraints are to be developed. Z may contain multiple examples of measurement process signals, e.g. several spectra of air with varying water vapor and carbon dioxide levels. The matrix Z is first orthogonalized relative to $U_p$.

$$Z' = Z - Z(Z^t U_p^t)$$

The singular value decomposition of Z' is then calculated $$Z' = U_z \Sigma_z V_z^t$$

If z' is the number of experimental measurement process signals being modeled, then the first z' columns of $U_z$ are then combined with the $U_p$ to form the f by p+z' matrix U . Note, for example, if z=10 spectra of air with varying levels of water vapor and carbon dioxide where used in Z, then only z'=2 columns of $U_z$ would be used since only two different process singals are being modeled.

5.0 Spectral Ranges:

The spectral data used in developing a Constrained Spectral Regression model may include all of the data points (frequencies or wavelengths) between the normal starting and ending points of a spectrometer scan, or it may be limited to subregions of the spectra, so as to exclude portions of the data. For many spectrometer systems, absorbances above a certain nominal value do not scale linearly with pathlength or component concentration. Since the regression models assume linear responce, regions where the absorbance exceeds the range of linear spectrometer response will generally be excluded from the data prior to the development of the model. Subregions can also be excluded to exclude measurement process signals that occur in narrow spectral ranges. For example, in the mid-infrared data where sample components are expected to absorb minimally in the 2300–2400 cm$^{-1}$ range, this spectral range may be excluded to avoid the necessity of adding a carbon dioxide spectrum as a correction spectrum.

We claim:

1. A method for recalibrating an analyzer which uses a correlation between calibration sample spectra and a property and/or composition data for estimating that property and/or composition data of a test sample, comprising
   (a) performing a spectral measurement on the test sample,
   (b) determining the property and/or composition data of the test sample from its measured spectrum, the determination being made from the correlation of the calibration sample spectra to said known property and/or composition data of the calibration sample,
   (c) comparing calibration sample spectra as to whether or not the measured spectrum is within the range of the calibration sample spectra,
   (d) isolating the test sample if said measured spectrum is not within the correlation between said calibration sample spectra and the property and/or composition data,
   (e) analyzing said test sample of step (d) by a separate method to ascertain the property and/or composition data, and
   (f) recalibrating the analyzer with this data and with the spectral measurement data obtained by performing the spectral measurement on the test sample of step (d).

2. A method as claimed in claim 1, wherein the spectral measurement of the test sample is performed in the infrared region.

3. A method as claimed in claim 1 for which the calibration sample is eigenvector-based, wherein a simulated spectrum for the test sample is determined by deriving the coefficients for the measured test spectrum from the dot products of the measured test spectrum with each of the model eigenspectra and by adding together the model eigenspectra scaled by the corresponding coefficients, and wherein a comparison is made between the simulated spectrum and the measured spectrum as an estimation of whether or not the measured spectrum is within the range of the calibration sample spectra in the model.

4. A method as claimed in claim 3, wherein the comparison between the simulated spectrum and the measured spectrum is made by determining a residual spectrum as the difference between the simulated spectrum and the measured spectrum, by calculating the Euclidean norm by summing the squares of the magnitudes of the residual spectrum at discrete frequencies, and by evaluating the magnitude of the Euclidean norm.

5. A method as claimed in claim 3, wherein data in the calibration sample spectra due to the measurement process itself is removed therefrom prior to defining the calibration by orthogonalizing the calibration sample spectra to one or more spectra modelling the measurement process data.

6. A method as claimed in claim 3, wherein the Mahalanobis distance is determined for the measured spectrum and the test sample is isolated if the magnitude of the determined Mahalanobis distance is indicative that the estimate of property and/or composition data of the test sample is an extrapolation from the range of data covered by the calibration samples.

7. A method as claimed in claim 6, further comprising calculating the Euclidean norm derived for each test sample/calibration sample pair and comparing the calculated Euclidean norms with a predetermined threshold value so as to isolate the test sample if said threshold value is exceeded.

8. A method as claimed in claim 3, wherein the spectral measurement performed on the test sample is carried out as an on-line spectral measurement.

9. A method as claimed in claim 3, wherein said test sample is a hydrocarbon test sample.

10. A method as claimed in claim 9, wherein said sample is a hydrocarbon/water mixture and the estimate is an estimate of the water content of said mixture.

11. A method as claimed in claim 9, wherein said sample is a hydrocarbon/water mixture and the estimate is an estimate of the hydrocarbon content of said mixture.

12. Apparatus for estimating property and/or composition data of a hydrocarbon test sample, which includes a means for recalibration, said apparatus comprising:
  (a) spectrometer means for performing a spectral measurement on a test sample;
  (b) computer means (i) for estimating the property and/or composition data of the test sample from its measured spectrum, the determination being made from the correlation of calibration sample spectra to known property and/or composition data for those calibration samples; (ii) for determining, on the basis of a check of the measured spectrum against the calibration sample spectra, whether or not the measured spectrum is within the range of the calibration sample spectra;
  (c) means for generating a response to negative results by isolating said test sample;
  (d) means for analyzing said test sample of step (c) to ascertain its property and/or composition data; and
  (e) means for inputting such data inputted to said computer for storage therein, so that the analyzer thereby becomes updated according to such data.

* * * * *